US012285481B2

United States Patent
Niazi et al.

(10) Patent No.: US 12,285,481 B2
(45) Date of Patent: Apr. 29, 2025

(54) METHODS FOR THE TREATMENT OF COVID-19 COMPRISING ADMINISTERING REPLICATION-DEFECTIVE ADENOVIRUSES ENCODING THE SARS-COV-2 SPIKE GLYCOPROTEIN AND MODIFIED NUCLEOCAPSID PROTEIN

(71) Applicant: NantCell, Inc., Culver City, CA (US)

(72) Inventors: Kayvan Niazi, Culver City, CA (US); Thomas H. King, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 0 days.

(21) Appl. No.: 18/312,532

(22) Filed: May 4, 2023

(65) Prior Publication Data

US 2023/0302121 A1 Sep. 28, 2023

Related U.S. Application Data

(63) Continuation of application No. 16/883,263, filed on May 26, 2020, now Pat. No. 11,684,668.

(Continued)

(51) Int. Cl.
*A61K 39/215* (2006.01)
*C07K 14/005* (2006.01)
(Continued)

(52) U.S. Cl.
CPC .......... *A61K 39/215* (2013.01); *C07K 14/005* (2013.01); *C07K 14/165* (2013.01); *C12N 1/16* (2013.01); *C12N 15/86* (2013.01); *A61K 38/00* (2013.01); *A61K 39/235* (2013.01); *C07K 14/8103* (2013.01); *C07K 2317/52* (2013.01); *C07K 2319/01* (2013.01);
(Continued)

(58) Field of Classification Search
CPC .................. A61K 39/215; C12N 15/86; C12N 2710/10341; C12N 2770/20034; C07K 2319/01
See application file for complete search history.

(56) References Cited

U.S. PATENT DOCUMENTS

| 6,133,036 A | 10/2000 | Putcha et al. |
| 6,716,392 B1 | 4/2004 | Putcha et al. |

(Continued)

FOREIGN PATENT DOCUMENTS

| CN | 1488646 A | 4/2004 |
| CN | 1572875 A | 2/2005 |

(Continued)

OTHER PUBLICATIONS

Nilvebrant, J., and J. Rockberg, 2018, An introduction to epitope mapping, Meth. Mol. Biol. 1785:1-10.*

(Continued)

*Primary Examiner* — Jeffrey S Parkin
(74) *Attorney, Agent, or Firm* — Martin Fessenmaier; Umberg Zipser LLP

(57) ABSTRACT

Compositions and methods are presented for prevention and/or treatment of a coronavirus disease wherein the composition comprises comprises a recombinant entity. The recombinant entity comprises a nucleic acid that encodes a nucleocapsid protein of coronavirus 2 (CoV2); and/or wherein the recombinant entity encodes a spike protein of CoV2.

12 Claims, 5 Drawing Sheets

Specification includes a Sequence Listing.

Related U.S. Application Data

(60) Provisional application No. 63/022,146, filed on May 8, 2020, provisional application No. 63/016,241, filed on Apr. 27, 2020, provisional application No. 63/016,048, filed on Apr. 27, 2020, provisional application No. 63/010,010, filed on Apr. 14, 2020, provisional application No. 63/009,960, filed on Apr. 14, 2020, provisional application No. 62/991,504, filed on Mar. 18, 2020, provisional application No. 62/988,328, filed on Mar. 11, 2020.

(51) Int. Cl.
| | | |
|---|---|---|
| *C07K 14/165* | (2006.01) | |
| *C12N 1/16* | (2006.01) | |
| *C12N 15/86* | (2006.01) | |
| *A61K 38/00* | (2006.01) | |
| *A61K 39/235* | (2006.01) | |
| *C07K 14/81* | (2006.01) | |

(52) U.S. Cl.
CPC ............. *C07K 2319/06* (2013.01); *C12N 2710/10341* (2013.01); *C12N 2770/20034* (2013.01); *C12Y 304/17023* (2013.01)

(56) References Cited

U.S. PATENT DOCUMENTS

| | | |
|---|---|---|
| 7,618,817 B2 | 11/2009 | Campbell |
| 7,750,123 B2 | 7/2010 | Marasco et al. |
| 8,034,332 B2 | 10/2011 | Klingemann |
| 8,313,943 B2 | 11/2012 | Campbell |
| 9,150,636 B2 | 10/2015 | Campbell |
| 9,181,322 B2 | 11/2015 | Campbell |
| 10,695,417 B2 * | 6/2020 | Jones ............... A61K 38/19 |
| 10,953,089 B1 | 3/2021 | Smith et al. |
| 11,104,916 B2 | 8/2021 | Jones et al. |
| 2004/0161388 A1 | 8/2004 | Liu et al. |
| 2005/0003548 A1 | 1/2005 | Korokhov et al. |
| 2006/0171962 A1 | 8/2006 | Enjuanes Sanchez et al. |
| 2007/0105193 A1 | 5/2007 | Vilalta et al. |
| 2010/0150923 A1 | 6/2010 | Jiang et al. |
| 2010/0196411 A1 | 8/2010 | Duke et al. |
| 2012/0076820 A1 | 3/2012 | Amara et al. |
| 2012/0107347 A1 | 5/2012 | Hodge et al. |
| 2012/0288502 A1 | 11/2012 | Diskin et al. |
| 2013/0123136 A1 | 5/2013 | Abassi et al. |
| 2016/0076053 A1 | 3/2016 | Jones et al. |
| 2016/0168591 A1 | 6/2016 | Brennan et al. |
| 2016/0223564 A1 | 8/2016 | Lee et al. |
| 2017/0224794 A1 | 8/2017 | Franzusoff et al. |
| 2017/0246276 A1 | 8/2017 | Palena et al. |
| 2018/0244756 A1 | 8/2018 | Graham et al. |
| 2018/0296663 A1 | 10/2018 | Hipp et al. |
| 2018/0306814 A1 | 10/2018 | Kulshrestha et al. |
| 2019/0307819 A1 | 10/2019 | Drew et al. |
| 2020/0054730 A1 * | 2/2020 | Niazi ............... C07K 14/70596 |
| 2020/0164058 A1 | 5/2020 | Hashem |
| 2021/0283245 A1 | 9/2021 | Niazi et al. |
| 2021/0284713 A1 | 9/2021 | Niazi et al. |
| 2021/0284716 A1 | 9/2021 | Niazi et al. |
| 2021/0371822 A1 | 12/2021 | Chaudhary |
| 2022/0016234 A1 | 1/2022 | Rice et al. |

FOREIGN PATENT DOCUMENTS

| | | | |
|---|---|---|---|
| CN | 102844329 | A | 12/2012 |
| CN | 111249454 | A | 6/2020 |
| CN | 111254155 | A | 6/2020 |
| CN | 111330003 | A | 6/2020 |
| CN | 111375055 | A | 7/2020 |
| EP | 1508615 | A1 | 2/2005 |
| JP | 2008505114 | A | 2/2008 |
| JP | 2019521148 | A | 7/2019 |
| JP | 2021167805 | A | 10/2021 |
| KR | 101453923 | B1 | 10/2014 |
| KR | 20220006125 | A | 1/2022 |
| WO | 2003066820 | A2 | 8/2003 |
| WO | WO 03/066820 | A2 * | 8/2003 |
| WO | 2005120565 | A2 | 12/2005 |
| WO | 2006068663 | A2 | 6/2006 |
| WO | 2006113214 | A2 | 10/2006 |
| WO | 2009006479 | A2 | 1/2009 |
| WO | 2011129468 | A1 | 10/2011 |
| WO | 2012109404 | A1 | 8/2012 |
| WO | 2014031178 | A1 | 2/2014 |
| WO | 2016112188 | A1 | 7/2016 |
| WO | 2016116398 | A1 | 7/2016 |
| WO | 2018014008 | A1 | 1/2018 |
| WO | 2018140456 | A1 | 8/2018 |
| WO | 2018200389 | A1 | 11/2018 |
| WO | 2019143606 | A1 | 7/2019 |
| WO | 2020086745 | A1 | 4/2020 |
| WO | 2020219974 | A1 | 10/2020 |
| WO | 2021165448 | A1 | 8/2021 |
| WO | 2021183665 | A1 | 9/2021 |
| WO | 2021183717 | A1 | 9/2021 |
| WO | 2021188599 | A1 | 9/2021 |
| WO | 2021212021 | A2 | 10/2021 |
| WO | 2021248853 | A1 | 12/2021 |
| WO | 2021250467 | A2 | 12/2021 |
| WO | 2021254287 | A1 | 12/2021 |
| WO | 2022132625 | A1 | 6/2022 |

OTHER PUBLICATIONS

Sanchez-Trincado, J. L., et al., 2017, Fundamentals and methods for T- and B-cell epitope prediction, J. Immunol. Res. Article ID 2680160, pp. 1-14.*

Lavarone, C., et al., 2017, Mechanism of action of mRNA-based vectors, Exp. Rev. Vaccines 16(9):871-881.*

Robert-Guroff, M., 2007, Replicating and non-replicating viral vectors for vaccine development, Curr. Opin. Biotechnol. 18:546-556.*

Liniger, M., et al., 2008, Induction of neutralizing antibodies and cellular immune responses against SARS coronavirus by recombinant measles viruses, Vaccine 26:2164-2174.*

Wu, F., et al., Mar. 2020, A new coronavirus associated with human respiratory disease in China, Nature 579:265-269 and S1-15, published online Feb. 3, 2020.*

Wu, F., et al., Mar. 2020, Severe acute respiratory syndrome coronavirus 2 isolate Wuhan-Hu-1, complete genome, GenBank MN908947.3, pp. 1-12.*

Liniger, M., et al., 2008, Induction of neutralising antibodies and cellular immune responses against SARS coronavirus by recombinant measles virus, Vaccine 26:2164-2174.*

Enjuanes, L., et al., 2008, Vaccines to prevent severe acute respiratory syndrome coronavirus-induced disease, Vir. Res. 133:45-62.*

See, R. H., et al., 2006, Comparative evaluation of two severe acute respiratory syndrome (SARS) vaccine candidates in mice challenged with SARS coronavirus, J. Gen. Virol. 87:641-650.*

Chen et al., "Fusion protein linkers: property, design and functionality", Adv Drug Deliv Rev, vol. 65, No. 10, 32 pages.

Battle et al., "Soluble angiotensin-converting enzyme 2: a potential approach for coronavirus infection therapy?", Clinical Science, 2020, vol. 134, pp. 543-545.

Kruse Robert L., "Therapeutic strategies in an outbreak scenario to treat the novel coronavirus originating in Wuhan, China [version 2; peerreview: 2 approved]", F1000 Research, 2020, vol. 9, No. 7, 14 pages.

Lu et al., "Arg15-Lys17-Arg18 Turkey Ovomucoid Third Domain Inhibits Human Furin", The Journal of Biological Chemistry, 1993, vol. 268, No. 20, p. 14583-14585.

Coutard et al., "The spike glycoprotein of the new coronavirus 2019-nCOV contains a furin-like cleavage site absent in CoV of the same Glade", Antiviral Research, 2020, No. 176, 6 pages.

Yao et al., "Polyethyleneimine-coating enhances adenoviral transduction of mesenchymal stem cells", Biochemical and Biophysical Research Communications, 2014, vol. 447, No. 3, pp. 383-387.

(56) References Cited

OTHER PUBLICATIONS

Yin et al., "[Measurement of subsets of blood T lymphocyte in 93 patients with severe acute respiratory syndrome and its clinical significance]", Chinese Journal of Tuberculosis and Respiratory Diseases, 2003, vol. 26, No. 6, 1 page.
Lei et al., "Potent neutralization of 2019 novel coronavirus by recombinant ACE2-Ig", bioRxiv, 2020, 11 pages.
Amalfitano et al., "Production and Characterization of Improved Adenovirus Vectors with the E1, E2b, and E3 Genes Deleted", Journal of Virology, 1998, vol. 72, No. 2, pp. 926-933.
Yan et al., "Structural basis for the recognition of the SARS-CoV-2 by full-length human ACE2", Science, 2020, pp. 1-9.
Zhang et al."Angiotensin-converting enzyme 2(ACE2) as a SARS-CoV-2 receptor: molecular mechanisms and potential therapeutic target", Intensive Care Med, 2020, 5 pages.
Zhonghua Yi Xue Za Zhi, "Dynamic Changes of T-lymphocytes and Immunoglobulins in Patients With Severe Acute Respiratory Syndrome", Natl Med J China, Jun. 25, 2003, vol. 83, No. 12, pp. 1014-1017.
"The Involvement of Natural Killer Cells in thePathogenesis of Severe Acute Respiratory Syndrome", National Research Project for SARS, Beijing Group, American Journal of Clinical Pathology, 2004, vol. 121, pp. 507-511.
Bergamaschi et al., "Intracellular Interaction of Interleukin-15 with Its Receptor alpha during Production Leads to Mutual Stabilization andIncreased Bioactivity", The Journal of Biological Chemistry, 2008, vol. 283, No. 7, pp. 4189-4199.
Bessard et al., "High Antitumor Activity of RLI, an interleukin-15 (IL-15)-IL-15 Receptor Alpha Fusion Protein, in Metastatic Melanoma and Colorectal Cancer", Mal Cancer Ther, 2009, vol. 8, No. 9, pp. 2736-2745.
Chan et al., "A familial cluster of pneumonia associated with the 2019 novel coronavirus indicating person-to-person transmission: a study of a family cluster", lancet, vol. 395, pp. 514-523.
Clay et al., "Severe Acute Respiratory Syndrome-Coronavirus Infection in Aged Nonhuman Primates Is Associated With Modulated Pulmonary and Systemic Immune Responses", Immunity & Ageing, 2014, vol. 11, No. 4, pp. 1-16.
Dubois et al., "Preassociation of IL-15 With IL-15R alpha-IgG1-Fc Enhances Its Activity on Proliferation of NK and CD8+/CD44high T cells and its antitumor action", The Journal of Immunology, 2008, vol. 180, pp. 2099-2106.
Duitman et al., "How a Cytokine Is Chaperoned Through the Secretory Pathway by Complexing With Its Own Receptor: Lessons From interleukin-15 (IL-15)/IL-15 Receptor Alpha", molecular and Cellular Biology, Aug. 2008, vol. 28, No. 15, pp. 4851-4861.
Ellis-Connell et al., "ALT-803 Transiently Reduces Simian Immunodeficiency Virus Replication in the Absence of Akritiretroviral Treatment", Journal of Virology, 2018, vol. 92, No. 3, pp. 1-21.
Epardaud et al., "Interleukin-15/interleukin-15R Alpha Complexes Promote Destruction of Established Tumors by Reviving Tumor-Resident CD8+ T Cells", Cancer Research, 2008, vol. 68, No. 8, pp. 2972-2983.
Fehniger et al., "Interleukin-2 and interleukin-15: Immunotherapy for Cancer", Cytokine Growth Factor Rev, 2002, vol. 13, No. 2, pp. 169-183.
Furuya et al., "Effectiveness of two different dose administration regimens of an IL-15 superagonist complex (ALT-803) in an orthotopic bladder cancer mouse model", Journal of translational Medicine, 2019, vol. 17, No. 29, pp. 1-12.
Gomes-Giacoia et al., "Intravesical ALT-803 and BCG Treatment Reduces Tumor Burden in a Carcinogen Induced Bladder Cancer Rat Model; A Role for Cytokine Production and NK Cell Expansion", Plos One, 2014, vol. 9, No. 6, pp. 1-11.
Guan et al., "Clinical Characteristics of Coronavirus Disease 2019 in China", The New England Journal of Medicine, 2020, 13 pages.
Guilliams et al., "The function of Fc gamma receptors in dendritic cells and macrophages", Nature Reviews Immunology, 2014, vol. 14, pp. 94-108.

Huang et al., "Clinical features of patients infected with 2019 novel coronavirus in Wuhan, China", Lancet, 2020, vol. 395, No. 10223, pp. 1-10.
Huntington et al., "IL-15 transpresentation promotes both human T-cell reconstitution and T-cell-dependent antibody responses in vivo", Proceedings of the National Academy of Sciences, 2011, vol. 108, No. 15, pp. 6217-6222.
Jones et al., "A Subset of Latency-Reversing Agents Expose HIV-Infected Resting CD4+ T-Cells to Recognition by Cytotoxic T-Lymphocytes", Plos Pathogens, 2016, pp. 1-25.
Kim et al., "IL-15 superagonist/IL-15RaSushi-Fc Fusion Complex (IL-15SA/IL-15RaSu-Fc; ALT-803) Markedly Enhances Specific Subpopulations of NK and Memory CD8+ T Cells, and Mediates Potent Anti-Tumor Activity Against Murine Breast and Colon Carcinomas", Oncotarget, 2016, vol. 7, No. 13, 16130-16145.
Law et al., "Chemokine Up-Regulation in SARS-coronavirus-infected, Monocyte-Derived Human Dendritic Cells", Blood, 2005, vol. 106, No. 7, pp. 2366-2374.
Mah et al., "Glycolytic Requirement for NK Cell Cytotoxicity and Cytomegalovirus Control", JCI Insight, 2017, vol. 2, No. 23, 18 pages.
Margolin et al., "Phase 1 Trial of ALT-803, A Novel Recombinant IL15 Complex, in Patients With Advanced Solid Tumors", Clinical Cancer Research, 2018, vol. 24, No. 22, pp. 555-5561.
Mathias et al., "Therapeutic Administration of IL-15 Superagonist Complex ALT-803 Leads to Long-Term Survival and Durable Antitumor Immune Response in a Murine Glioblastoma Model", International Journal of Cancer, 2016, vol. 138, pp. 187-194.
Mcbrien et al., "Robust and persistent reactivation of SIV and HIV by N-803 and depletion of CD8+ cells", Nature, Feb. 6, 2020, vol. 578, pp. 154-159.
Mortier et al., "Soluble Interleukin-15 Receptor a (IL-15Ra)-sushi as a Selective and Potent Agonist of IL-15 Action through IL-15R(3/y Hyperagonist IL-15-IL-15Ra Fusion Proteins", Journal of Biological Chemistry, 2006, vol. 281, No. 3, pp. 1612-1619.
Rhode et al., "Comparison of the Superagonist Complex, ALT-803, to IL15 as Cancer Immunotherapeutics in Animal Models", Cancer Immunol Res, 2016, vol. 4, pp. 1-12.
Romee et al., "First-in-human Phase 1 Clinical Study of the IL-15 Superagonist Complex ALT-803 to Treat Relapse After Transplantation", Blood, 2018, vol. 131, No. 23, pp. 2515-2527.
Rosario et al., "The IL-15-Based ALT-803 Complex Enhances FcyRIIIa-Triggered NK Cell Responses and In Vivo Clearance of B Cell Lymphomas", Clinical Cancer Research, 2016, vol. 22, No. 3, pp. 596-608.
Seay et al., "In Vivo Activation of Human NK Cells by Treatment With an Interleukin-15 Superagonist Potently Inhibits Acute In Vivo HIV-1 Infection in Humanized Mice", Journal of Virology, 2015, 46 pages.
Spiegel et al., "Inhibition of Beta Interferon Induction by Severe Acute Respiratory Syndrome Coronavirus Suggests a Two-Step Model for Activation of Interferon Regulatory Factor 3", Journal of Virology, 2005, vol. 79, No. 4, pp. 2079-2086.
Waldmann Thomas A., "The biology of interleukin-2 and interleukin-15: implications for cancer therapy and vaccine design", Nature Reviews Immunology vol. 2006, vol. 6, pp. 595-601.
Wang et al., "IgG Fc engineering to modulate antibody effector functions", 2017, 11 pages.
Webb et al., "The human IL-15 superagonist ALT-803 directs SIV-specific CD8+ T cells into B-cell follicles", Blood Advances, 2018, vol. 2, No. 2, pp. 76-84.
Weiss et al., "Coronavirus Pathogenesis and the Emerging Pathogen Severe Acute Respiratory Syndrome Coronavirus", Microbiology and molecular Biology Reviews, 2005, vol. 69, No. 4, 31 pages.
Wrangle et al., "ALT-803, an IL-15 Superagonist, in Combination With Nivolumab in Patients With Metastatic Non- Small Cell Lung Cancer: A Non-Randomised, Open-Label, Phase 1 b Trial", Lancet Oncol, 2018, vol. 19, No. 5, pp. 1-11.
Xu et al., "Efficacy and Mechanism-Of-Action of a Novel Superagonist interleukin-15: Interleukin-15 Receptor aSu/Fc Fusion Complex in Syngeneic Murine Models of Multiple Myeloma", Cancer Research, 2013, vol. 73, No. 10, pp. 3075-3086.

(56) References Cited

OTHER PUBLICATIONS

Zhu et al. "Novel Human Interleukin-15 Agonists", The Journal of Immunology, 2009, vol. 183, pp. 3598-3607.
Zhu et al., "MHC Class I-Related Neonatal Fc Receptor for IgG Is Functionally Expressed in Monocytes, Intestinal Macrophages, and Dendritic Cells", The Journal of immunology, 2001, vol. 166, pp. 3266-3276.
Saiki et al., "Induction of Humoral Responses Specific for Paraneoplastic Cerebellar Degeneration-Associated Antigen by Whole Recombinant Yeast Immunization", Journal of Autoimmunity, 2005, vol. 24, pp. 203-208.
Lei et al., "Yeast Surface-Displayed H5N1 Avian Influenza Vaccines", Hindawi publishing Corporation, 2016, pp. 1-12.
Kim et al., "Oral Immunization With Whole Yeast Producing Viral Capsid Antigen Provokes a Stronger Humoral Immune Response Than Purified Viral Capsid Antigen", Letters in Applied Microbiology, 2013, vol. 58, pp. 285-291.
Safdari et al., "Use of Single-Chain Antibody Derivatives for Targeted Drug Delivery", Molecular Medicine, 2016, vol. 22, pp. 258-270.
"Sorrento Develops STI-4398 (COVIDTRAPTm PROTEIN) for Potential Prevention and Treatment of SARS-COV-2 Coronavirus Disease (COVID-19)", Sorrento Therapeutics, 2020, 4 pages.
Levin et al. Fc fusion as a platform technology: potential for modulating immunogenicity. Trends Biotechnol. Jan. 2015;33(1):27-34.
Renegar et al. Role of IgA versus IgG in the Control of Influenza Viral Infection in the Murine Respiratory Tract. J Immunol. 2004; 173:1978-1986.
Raftery et al., "Chitosan for Gene Delivery and Orthopedic TissueEngineering Applications", Molecules, 2013, vol. 18, pp. 5611-5647.
Cunningham et al., "Effective Long-term Preservation of Biological Evidence", Bode Technology, 2014, 153 pages.
Roth et al., "Functionalized Calcium Carbonate Microparticles for the Delivery of Proteins", European Journal of Pharmaceutic,s and Biopharmaceutics, 2017, 38 pages.
Rogers et al., "Isolation of potent SARS-COV-2 neutralizing antibodies and protection from disease in a small animal model", Science, 2020, 12 pages.
Wec et al., "Broad sarbecovirus neutralizing antibodies define a key site of vulnerability on the SARSCOV-2 spike protein", Version 2. bioRxiv., 2020, 18 pages.
Yuan et al., "A highly conserved cryptic epitope in the receptor binding domains of SARS-CoV-2 and SARS-CoV", Science, 2020, vol. 368, pp. 1-4.
Glasgow et al., "Engineered ACE2 receptor traps potently neutralize SARS-COV-2", PNAS, 2020, 25 pages.
Rice et al., "A Next Generation Bivalent Human Ad5 COVID-19 Vaccine Delivering Both Spike and Nucleocapsid Antigens Elicits Th1 Dominant CD4+, CD8+ T-cell and Neutralizing Antibody Responses", BioRxiv, 2020, 36 pages.
UniProtKB—Q9BYF1 (ACE2 H U Man), Aug. 2, 2005.
See et al., "Comparative evaluation of two severe acute respiratory syndrome (SARS) vaccine candidates in mice challenged with SARS coronavirus", Journal of General Virology, 2006, vol. 87, pp. 641-650.
Sieling et al., "Th1 Dominant Nucleocapsid and Spike Antigen-Specific CD4+ and CD8+ Memory T CellRecall Induced by hAd5 S-Fusion + N-ETSD Infection of Autologous Dendritic Cells fromPatients Previously Infected with SARS-CoV-2", Medrxiv the preprint server for health sciences, 2020, 44 pages.
Gabitzsch et al., "Complete Protection of Nasal and Lung Airways Against SARS-CoV-2 Challengeby Antibody Plus Th1 Dominant N- and S-Specific T-Cell Responses to SubcutaneousPrime and Thermally-Stable Oral Boost Bivalent hAd5 Vaccination in an NHP Study", Biorxiv the preprint server for biology, 2020, 31 pages.
Seif et al., "Yeast (Saccharomyces cerevisiae) Polarizes Both M-CSF- and GM-CSF-Differentiated Macrophages Toward an M1-Like Phenotype", Inflammation, 2016, 14 pages.

Biondo et al., "Recognition of yeast nucleic acids triggers a host-protective type I interferon response", Eur. J. Immunol., 2011, vol. 41, pp. 1969-1979.
International Search Report and Written Opinion received for PCT Application Serial No. PCT/IB2021/054887 dated Sep. 6, 2021, 13 pages.
Khodaei et al., "Covalent Immobilization of Protein A on Chitosan and Aldehyde Double-Branched Chitosan as Biocompatible Carriers for Immunoglobulin G (Igg) Purification", Journal of Chromatographic Science, 2018, pp. 1-8.
Byrnes et al., "A SARS-CoV-2 serological assay to determine the presence of blocking antibodies that compete for human ACE2 binding", medRxiv, 2020, 23 pages.
Wang et al., "A human monoclonal antibody blocking SARS-COV-2 infection", Nature Communications, 2020, vol. 11, No. 2251, pp. 1-6.
International Search Report and Written Opinion received for PCT Application Serial No. PCT/US2021/021737 dated Jun. 25, 2021, 11 pages.
Zhao et al., "Identification and characterization of dominant helper T-cell epitopes in the nucleocapsid protein of severe acute respiratory syndrome coronavirus", Journal of Virology, 2007, vol. 81, No. 11, pp. 6079-6088.
Gabitzsch et al., "Anti-tumor immunotherapy despite immunity to adenovirus using a novel adenoviral vector Ad5 [EI-, E2b-]-CEA", Cancer Immunology Immunotherapy, 2010, vol. 59, pp. 1131-1135.
Fan et al., "The nucleocapsid protein of coronavirus infectious bronchitis virus: crystal structure of its N-terminal domain and multimerization properties", Structure, 2005, vol. 13, pp. 1859-1868.
International Search Report and Written Opinion received for PCT Application Serial No. PCT/US2021/021819 dated Jun. 21, 2021, 20 pages.
Oi-Wing et al.,"Substitution at Aspartic Acid 1128 in the SARSCoronavirus Spike Glycoprotein Mediates Escape from aS2 Domain-Targeting Neutralizing Monoclonal Antibody", Plos one, 2014, vol. 9, No. 7, pp. 1-11.
Pak et al., "Structural Insights into Immune Recognition of theSevere Acute Respiratory Syndrome Coronavirus SProtein Receptor Binding Domain", Journal of Molecular Biology, 2009, vol. 388, pp. 815-823.
Park et al., "Spike protein binding prediction with neutralizing antibodies of SARS-COV-2", bioRxiv , 2020, 22 pages.
Tripp et al., "Monoclonal antibodies to SARS-associated coronavirus (SARS-CoV): Identification of neutralizing and antibodies reactive to S, N, M and E viral proteins", Journal of Virological Methods, 2005, vol. 128, pp. 21-28.
Zheng et al., "Monoclonal antibodies for the S2 subunit of spike of SARS-CoV-1 cross-react with the newly-emerged SARS-CoV-2", Eurosurveillance, 2020, vol. 25, No. 28, pp. 19-28.
Pietravalle et al., "Cleavage of membrane-bound CD40 ligand is not required for inducing B cell proliferation and differentiation", Eur. J. Immunol, vol. 26, 1996, pp. 725-728.
Tan, Y. W., et al., Amino acid residues critical for RNA-binding in the N-terminal domain of the nucleocapsid protein are essential determinants for the infectivity of coronavirus in cultured cells, Nucleic Acids Res. 34(17): 4816-4825.
Lin, H.- X., et al., 2008, Identification of residues in the receptor-binding domain (RBD) of the spike protein of human coronavirus NL63 that are critical for the RBD-ACE2 receptor interaction, J. Gen. Virol. 89:1015-1024.
Lu, Y., et al., 2008, Importance of SARS-CoV spike protein Trp-rich region in viral infectivity, Biochem. Biophys. Res. Comm. 371: 356-360.
Guo, Y., et al., 2009, Identification of a new region of Sars-CoV S protein critical for viral entry, J. Mol. Biol. 394:600-605.
Bhatti, J. S., et al., Nov. 2020, Therapeutic Strategies in the Development of Anti-viral Drugs and Vaccines Against SARS-CoV-2 Infection, Mol. Neurobiol., DOI: 10. 1007/s12035-020-02074-2, published online Aug. 18, 2020, pp. 1-22.
Rice et al., "Intranasal plus subcutaneous prime vaccination with a dual antigen COVID 19 vaccine elicits T cell and antibody responses in mice" Scientific Reports, (2021) 11:14917 p. 1-15.

(56) References Cited

OTHER PUBLICATIONS

Zhou, W., et al., 2023, Vaccines' New Era-RNA Vaccine, Viruses 15, 1760, pp. 1-19.
International Preliminary Report on Patentability received for PCT Application Serial No. PCT/IB2021/054887 dated Feb. 2, 2023, 6 pages.
International Preliminary Report on Patentability received for PCT Application Serial No. PCT/US2021/021737 dated Sep. 6, 2022, 6 pages.
Office Action received in Canada Patent Application Serial No. 3170513 dated Aug. 21, 2023, 5 pages.
Office Action received in Canada Patent Application Serial No. 3170513 dated Oct. 22, 2024, 3 pages.
Extended European Search Report received in European Patent Application Serial No. 21768699.7 dated Mar. 18, 2024, 15 pages.
Enjuanes, L. et al. (2008) Vaccines to prevent severe acute respiratory syndrome coronavirus-induced disease. Virus Research, vol. 133, No. 1, 45-62, ISSN: 0168-1702, DOI: 10.1016/J.VIRUSRES.2007.01.021.
Shi, J. et al. (2015) Epitope-based vaccine target screening against highly pathogenic Mers-CoV: an in silico approach applied to emerging infectious diseases. PLOS ONE, vol. 10, No. 12, e0144475, US ISSN: 1932-6203, DOI: 10.1371/journal.pone.0144475.
Abdelzaher, H. M., et al., 2021, RNA Vaccines against Infectious Diseases: Vital Progress with Room for Improvement, Vaccines 9: 1-23.
Partial Supplementary European Search Report received in European Patent Application Serial No. 21846127.5 dated Aug. 2, 2024, 14 pages.
Bosnjak Berislav et al.: "Low serum neutralizing anti-SARS-COV-2 S antibody levels in mildly affected COVID-19 convalescent patients revealed by two different detection methods", Cellular & Molecular Immunology, vol. 18, No. 4, Nov. 2, 2020 (Nov. 2, 2020), pp. 936-944, XP037390037, ISSN: 1672-7681, DOI:10.1038/S41423-020-00573-9.
Abe Kento T. et al.: "A simple protein-based surrogate neutralization assay for SARS-CoV-2", JCI Insight, vol. 5, No. 19, Oct. 2, 2020 (Oct. 2, 2020), XP055780531, ISSN: 2379-3708, DOI: 10.1172/jci.insight.142362 Retrieved from the Internet: URL:https://www.ncbi.nlm.nih.gov/pmc/articles/PMC7566699/pdf/jciinsight-5-142362.pdf.
Edward P. Gniffke et al.: "Plasma from recovered COVID19 subjects inhibits spike protein binding to ACE2 in a microsphere-based inhibition assay.", MEDRXIV, Jun. 11, 2020 (Jun. 11, 2020), XP055769440, DOI: 10.1101/2020.06.09.20127050 Retrieved from the Internet: URL:https://www.medrxiv.org/content/10.1101/2020.06.09.20127050v1.full.pdf>.
Tan Chee Wah et al.: "A SARS-COV-2 surrogate virus neutralization test based on antibody-mediated blockage of ACE2-spike protein-protein interaction", Nature Biotechnology, Nature Publishing Group US, New York, vol. 38, No. 9, Jul. 23, 2020 (Jul. 23, 2020), pp. 1073-1078, XP037237853, ISSN: 1087-0156, DOI: 10.1038/S41587-020-0631-Z [retrieved on Jul. 23, 2020].
Extended European Search Report received in European Patent Application Serial No. 21846127.5 dated Nov. 5, 2024, 16 pages.
Rosales-Mendoza Sergio et al.: "What Does Plant-Based Vaccine Technology Offer to the Fight against COVID-19?", Vaccines, vol. 8, No. 2, Apr. 14, 2020 (Apr. 14, 2020), p. 183, XP093151469, CH ISSN: 2076-393X, DOI: 10.3390/vaccines8020183.
Wang Ning et al.: "Aluminum Nanoparticles Acting as a Pulmonary Vaccine Adjuvant-Delivery System (VADS) Able to Safely Elicit Robust Systemic and Mucosal Immunity", Journal of Inorganic and Organometallic Polymers and Materials, Springer US, New York, vol. 30, No. 10, May 9, 2020 (May 9, 2020), pp. 4203-4217, XP037246387, ISSN: 1574-1443, DOI: 10.1007/S10904-020-01572-Z [retrieved on May 9, 2020].
First Examination Report received in Australia Patent Application Serial No. 2021236141 dated Apr. 9, 2024, 5 pages.
Notice of Acceptance for Patent Application received in Australia Patent Application Serial No. 2021236141 dated May 17, 2024, 3 pages.
First Examination Report received in Australia Patent Application Serial No. 2021312381 dated May 22, 2024, 4 pages.
Second Examination Report received in Australia Patent Application Serial No. 2021312381 dated Jun. 24, 2024, 5 pages.
Third Examination Report received in Australia Patent Application Serial No. 2021312381 dated Sep. 4, 2024, 3 pages.
Fourth Examination Report received in Australia Patent Application Serial No. 2021312381 dated Oct. 8, 2024, 8 pages.
Ali, Amanat, et al., Dynamics of the ACE2-SARS-CoV-2/SARS-CoV spike protein interface reveal unique mechanisms', 2020, Scientific reports, vol. 10(1), pages (2020), Article 14214.
Fukushi, Shuetsu., 'Competitive ELISA for the detection of serum antibodies specific for middle east respiratory syndrome coronavirus (MERS-COV)', 2020, Coronaviruses: Methods and Protocols, pp. 55-65.
Neumann MM, Volodkin D. Porous antibody-containing protein microparticles as novel carriers for ELISA. Analyst. Feb. 1, 20207;145(4): 1202-1206. doi: 10.1039/c9an01888c. PMID: 31859691.
Zhuang, Wei, et al. "Sensitive and portable electrochemical immunoassay for lipoprotein-associated phospholipase A 2 using BSA-doped $CaCO_3$ nanospheres to regulate pH readout." Analytical Methods 11.12 (2019): 1631-1638.
Peng J, Feng LN, Zhang K, Li XH, Jiang LP, Zhu JJ. Calcium carbonate-gold nanocluster hybrid spheres: synthesis and versatile application in immunoassays. Chemistry. Apr. 2, 20123;18(17):5261-8. doi: 10.1002/chem.201102876. Epub Mar. 1, 20125. PMID: 22422592.
Mou, Huihui et al. "Mutations from bat ACE2 orthologs markedly enhance ACE2-Fc neutralization of SARS-CoV-2." bioRxiv : the preprint server for biology 2020.06.29.178459. Jun. 30, 2020, doi: 10.1101/2020.06.29.178459. Preprint.
Request for the Submission of an Opinion received in Korea Patent Application Serial No. 10-2023-7006003 dated Oct. 25, 2024, 11 pages (including English Translation).
Seth J. zost et al., nature, (Jul. 15, 2020), vol. 584, and the pp. 443-449.
First Office Action received in China Patent Application Serial No. 202180020795.0 dated Jun. 19, 2024, 18 pages.
Notice of Reasons for Refusal received in Japan Patent Application Serial No. 2022-554944 dated Dec. 26, 2023, 11 pages.
Decision of Refusal received in Japan Patent Application Serial No. 2022-554944 dated Aug. 2, 2024, 6 pages.
Notice of Reasons for Refusal received in Japan Patent Application Serial No. 2023-503132 dated Aug. 13, 2024, 13 pages.
Lee, Y., et al., Oct. 2023, Immunogenicity of lipid nanoparticles and its impact on the efficacy of mRNA vaccines and therapeutics, Exp. Mol. Med. 55:2085-2096.
Hou, X., et al., Dec. 2021, Lipid nanoparticles for mRNA delivery, Nat. Rev. Mat. 6:1078-1094.
Sharon D., and A. Kamen, 2018, Advancements in the design and scalable production of viral gene transfer vectors, Biotechnology and Bioengineering, 115:25-40.
Second Office Action received in China Patent Application Serial No. 202180020795.0 dated Jan. 22, 2025, 9 pages.

* cited by examiner

Figure 6

SEQUENCE LISTING

```
Sequence total quantity: 5
SEQ ID NO: 1            moltype = AA  length = 473
FEATURE                 Location/Qualifiers
REGION                  1..473
                        note = Nucleocapsid protein
source                  1..473
                        mol_type = protein
                        organism = synthetic construct
SEQUENCE: 1
MSDNGPQNQR NAPRITFGGP SDSTGSNQNG ERSGARSKQR RPQGLPNNTA SWFTALTQHG   60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAPFGMSRI GMEVTPSGTW LTYTGAIKLD DKDPNFKDQV ILLNKHIDAY  360
KTFPPTEPKK DKKKKADETQ ALPQRQKKQQ TVTLLPAADL DDFSKQLQQS MSSADSTQAG  420
PGPGNLVPMV ATVGPGPGML IPIAVGGALA GLVLIVLIAY LIGKKHCSYQ DIL         473

SEQ ID NO: 2            moltype = AA  length = 27
FEATURE                 Location/Qualifiers
REGION                  1..27
                        note = N-ETSD
source                  1..27
                        mol_type = protein
                        organism = synthetic construct
SEQUENCE: 2
MLLLPFQLLA VLFPGGNSED YKDDDDK                                       27

SEQ ID NO: 3            moltype = DNA  length = 1552
FEATURE                 Location/Qualifiers
misc_feature            1..1552
                        note = DNA encoding ETSD and nucleocapsid proteins
source                  1..1552
                        mol_type = other DNA
                        organism = synthetic construct
SEQUENCE: 3
aatgctgctg ctgcccttcc agttgctggc tgtcctcttt cccggcggca actccgagga   60
ttacaaggac gacgacgaca agggtggagg ctctggaggt ggctctggtg gaggttccgg  120
tggcggatct atgagcgaca acggtcccca gaatcaaaga aatgcgccca gaattacatt  180
cggcggccct tctgatagca ctggctcaaa tcaaaacggg gagagaagcg gagccaggtc  240
```

```
caaacagcgg agaccccaag gcctgcctaa taacaccgct tcctggttca cagctctgac    300
gcaacacggc aaggaggatc tgaagtttcc acggggtcag ggcgtcccga ttaacacgaa    360
ctctagccca gatgaccaaa tagggtacta cagaagagcg acaaggcgga tcagaggagg    420
cgatggaaaa atgaaggatc tgtccccrag gtggtatttc tattacctgg cacaggccc    480
tgaagctggg ttgccttacg gcgcaaacaa agatgaatt atatgggtgg ccaccgaggg    540
ggcgttgaac accccaaagg atcacatcgg aacgaggaat cccgccaaca atgctgtat    600
agtgctccaa ctgccacagg gaacaaccct gcctaagggc ttctacgccg aggggagccg    660
cggtggcagc caggccagct ccagaagttc ctcccgcagc cggaacagct ctagaaacag    720
cactcccggc agctccagag ggacaagccc agccagaatg gccggcaatg gcggcgacgc    780
tgccctcgca cttctgttgc ttgatcggct caatcaactc gaaagcaaaa tgtccggcaa    840
gggacaacaa cagcaaggac agaccgttac aaaaaaaagc gccgccgagg ctagcaagaa    900
gcccagacag aagcgaaccg caacaaaggc ctataatgta acacaagcct tggaaggcg    960
gggacccgaa cagacccagg gaatttggg cgaccaggaa ctgatccggc aagggacaga   1020
ctataaacat tggccacaga tagcgcaatt tgctccctcc gcctccgcct tctttggcat   1080
gtcaagaata ggcatggaag taactccttc tggaacctgg ctgacgtaca ctggggcaat   1140
caagttggat gataaggacc ctaatttcaa ggaccaagtt atttgctca caagcatat   1200
agacgcctac aagactttcc cgcctaccga acctaaaaag gataagaaga gaaagcaga   1260
cgagacccag gccctgcctc aacggcaaaa gaagcgacaa actgtgacac tcctgcccgc   1320
cgctgacttg gatgatttt caaaacagct ccaacagagt atgagcagcg ccgatagac   1380
ccaagctgga ccgggtccgg gcaacctggt gccgatggtg gcgaccgtgg gtccaggacc   1440
gggtatgctg atccccatcg ccgtgggcgg ggccctggcc ggcctcgtgc tgatcgtcct   1500
tatcgcctac ctcatcggca gaagcactg ctcatatcag gacatcctgt ga           1552

SEQ ID NO: 4          moltype = AA  length = 1282
FEATURE               Location/Qualifiers
REGION                1..1282
                      note = spike protein
source                1..1282
                      mol_type = protein
                      organism = synthetic construct
SEQUENCE: 4
MFVFLVLLPL VSSYPYDVPD YAQCVNLTTR TQLPPAYTNS FTRGVYYPDK VFRSSVLHST    60
QDLFLPFFSN VTWFHAIHVS GTNGTKRFDN PVLPFNDGVY FASTEKSNII RGWIFGTTLD   120
SKTQSLLIVN NATNVVIKVC EFQFCNDPFL GVYYHKNNKS WMESEFRVYS SANNCTFEYV   180
SQPFLMDLEG KQGNFKNLRE FVFKNIDGYF KIYSKHTPIN LVRDLPQGFS ALEPLVDLPI   240
GINITRFQTL LALHRSYLTP GDSSSGWTAG AAAYYVGYLQ PRTFLLKYNE NGTITDAVDC   300
ALDPLSETKC TLKSFTVEKG IYQTSNFRVQ PTESIVRFPN ITNLCPFGEV FNATRFASVY   360
AWNRKRISNC VADYSVLYNS ASFSTFKCYG VSPTKLNDLC FTNVYADSFV IRGDEVRQIA   420
PGQTGKIADY NYKLPDDFTG CVIAWNSNNL DSKVGGNYNY LYRLFRKSNL KPFERDISTE   480
IYQAGSTPCN GVEGFNCYFP LQSYGFQPTN GVGYQPYRVV VLSFELLHAP ATVCGPKKST   540
NLVKNKCVNF NFNGLTGTGV LTESNKKFLP FQQFGRDIAD TTDAVRDPQT LEILDITPCS   600
FGGVSVITPG TNTSNQVAVL YQDVNCTEVP VAIHADQLTP TWRVYSTGSN VFQTRAGCLI   660
GAEHVNNSYE CDIPIGAGIC ASYQTQTNSP RRARSVASQS IIAYTMSLGA ENSVAYSNNS   720
IAIPTNFTIS VTTEILPVSM TKTSVDCTMY ICGDSTECSN LLLQYGSFCT QLNRALTGIA   780
VEQDKNTQEV FAQVKQIYKT PPIKDFGGFN FSQILPDPSK PSKRSFIEDL LFNKVTLADA   840
GFIKQYGDCL GDIAARDLIC AQKFNGLTVL PPLLTDEMIA QYTSALLAGT ITSGWTFGAG   900
AALQIPFAMQ MAYRFNGIGV TQNVLYENQK LIANQFNSAI GKIQDSLSST ASALGKLQDV   960
VNQNAQALNT LVKQLSSNFG AISSVLNDIL SRLDKVEAEV QIDRLITGRL QSLQTYVTQQ  1020
LIRAAEIRAS ANLAATKMSE CVLGQSKRVD FCGKGYHLMS FPQSAPHGVV FLHVTYVPAQ  1080
EKNFTTAPAI CHDGKAHFPR EGVFVSNGTH WFVTQRNFYE PQIITTDNTF VSGNCDVVIG  1140
IVNNTVYDPL QPELDSFKEE LDKYFKNHTS PDVDLGDISG INASVVNIQK EIDRLNEVAK  1200
NLNESLIDLQ ELGKYEQYIK WPWYIWLGFI AGLIAIVMVT IMLCCMTSCC SCLKGCCSCG  1260
SCCKFDEDDS EPVLKGVKLH YT                                          1282

SEQ ID NO: 5          moltype = DNA  length = 3850
FEATURE               Location/Qualifiers
misc_feature          1..3850
                      note = HA-spike
source                1..3850
                      mol_type = other DNA
                      organism = synthetic construct
SEQUENCE: 5
aatgttcgtt tttctcgttc tcctcccgct tgtgagcagc tatccgtatg atgtgccgga     60
ttatgcgcaa tgtgtcaacc tcaccacaag gacacagctc cctccgcat atacgaatag    120
ctttaccaga ggcgtatact atcctgataa ggtctttagg agctcagtac tgcatagcac    180
tcaggatctc ttcctgccgt tcttcagtaa tgttacttgg tttcacgcca ttcatgtttc    240
cgggaccaat ggcaccaaac ggttcgataa tccagtgctt cccttcaacg atgggtgta    300
cttrgccagc actgaaaaat ctaatataat tcggggatgg atttttcggaa ccacactcga    360
ttccaagact cagtccctct tgatcgttaa caacgctat aatgttgtca ttaaggtgtg    420
tgagtttcag ttctgcaacg accctttcct gggtgtctac taccataaaa ataacaagag    480
ctggatggag tccgaatttc gcgtctactc aagcgccaat aattgcactt ttgagtatgt    540
gtcccagccc ttttttgatg gatctggaggg aaagcagggc aatttcaaaa atctgagaga    600
attcgttttt aagaatatag atggatactt caaaatctac agcaaacaca cacccataaa    660
tcttgtggc gatcttcccc agggcttcag cgccgttgaa cccttgttg acttgacacc    720
aggcatcaac attaccaggt tccaaacgct gctcgccctc accgcagct acttgacacc    780
cggggattcc agctccggat ggaccgcgg cgccgcagcg tattatgtgg ggtacctgca    840
acccaggaca tttttgctca gtacaatga gaatgggacc atcacagatg cggtagactg    900
tgcactggat ccactcagcg aaactaaatg taccctgaaa gctttaccg tggagaaagg    960
aatctaccaa accagcaact tcagggtcca gcccactgaa tccatcgtta gatttcccaaa   1020
```

```
                                            -continued
tataactaat ttgtgtccat ttggagaggt gttcaatgct acaaggttcg cgtctgtata    1080
cgcttggaac cggaagcgca tctcaaattg cgtggctgat tatagcgttc tttacaacag    1140
cgcttccttt tccacgttca agtgctatgg tgtatccccg acaaagctga atgacttgtg    1200
cttcaccaat gtgtatgcgg attctttcgt tattcgaggc gatgaagtca gacaaattgc    1260
gcctggccag accggaaaga ttgccgacta caactataaa ctgccggacg actttactgg    1320
ttgcgtgatc gcttggaaca gcaataatct tgatagtaaa gttggaggaa actacaatta    1380
cctctataga ctgttcagaa agagcaactt gaagccattc gaacgggata tctctacgga    1440
gatctatcaa gctggcagca cccccctgcaa tggtgtggaa ggctttaatt gttattttcc    1500
tttgcagagc tatggcttcc aacctaccaa cggagtgggc taccagccct acagagtggt    1560
ggtgctcagc tttgaactgc tgcatgcccc ggccacagtt tgcgggccca aaaaaagcac    1620
gaatctggtt aagaacaaat gcgtcaactt caattttaat gggttgacag gtacaggcgt    1680
actgaccgaa tccaacaaaa agttcctgcc ttttcagcag ttcgggagag atatcgccga    1740
cactacagac gccgtcaggg atccccaaac actcgaaatt ctggacatca caccttgttc    1800
cttcggcggg gtatctgtga ttactccggg cacaaataccc agtaaccagg tagcggtgct    1860
ttaccaggat gtcaactgta cggaagtacc tgtcgctatt catgcggatc aactcactcc    1920
tacctggaga gtttattcca ctgggtccaa cgtgtttcag acccgagccg gctgcttgat    1980
tggcgcggaa catgttaaca actcctacga atgtgacatc cctatcggag ctggcatctg    2040
tgcttcctat caaacgcaaa cgaacagccc acggcgggcc agatccgtag cctctcaaag    2100
catcatcgct tatactatgt ccttgggggc tgaaaacagc gttgcctatt ccaacaatag    2160
catcgctatc cctaccaact ttaccatttc cgtgaccaca gaaatactgc cggtgagcat    2220
gacaaagact tctgtggact gtaccatgta tatatgcggc gatagcacag agtgttctaa    2280
tttgctgctg cagtacggca gcttttgtac ccaactcaac agagcactta cagggattgc    2340
cgtcgagcag gataaaaaca cccaggaggt tttcgcccag gttaagcaga tctacaagac    2400
cccaccaatc aaggatttcg gcggcttcaa tttttcccag atactgcccg atccttccaa    2460
gccatccaaa aggagcttta tagaggatct gctgttcaac aaggtgactc tggccgacgc    2520
tggctttatc aagcaatatg gcgattgcct ggggatatt gccgctaggg accttatctg    2580
cgctcaaaaa ttcaacggtc ttaccgttct cccgccctg ctcaccgacg agatgatagc    2640
ccagtacacg agcgcacttt tggccggcac gataaccagc ggctggacat tcggtgccgg    2700
ggccgctctt caaatcccct ttgccatgca gatggcctac agatttaatg ggataggcgt    2760
gacacaaaat gtcttgtatg aaaatcagaa actgattgca aaccagttta atagcgctat    2820
tggcaagatc caagatagcc ttttcctccac cgcatccgct ctgggaaagt tgcaagacgt    2880
cgtgaatcaa aacgcccaag ctctgaatac cctcgtgaag cagcttagct ccaactttgg    2940
cgcgatatcc tccgtgctga acgatatcct gtccagattg gacaaggtcg aggcagaagt    3000
ccagatcgat agattgataa ccggcagact ccagtctctg cagacatatg tgactcagca    3060
gttgataaga gcggccgaaa tacgagcgtc tgcaaatctc gcagcaacga aaatgtcaga    3120
gtgtgtattg gggcaaagta aaagagtaga tttctgtgga aagggttacc atctgatgtc    3180
attccccccag tctgcaccac atggagtagt ttttttgcat gtgacttatg tgcctgccca    3240
ggagaaaaat ttcaccactg cacctgcgat ctgtcatgac ggcaaggcac atttccctag    3300
agaaggcgtc ttcgtatcaa atggaacaca ctggtttgta acccaaagga acttttacga    3360
gccccaaatt ataactaccg acaacaccctt cgtaagcgga aactgcgacg tcgttatagg    3420
gatagtcaat aatacggtct atgaccctct tcagccggaa ctggactcct ttaaagaaga    3480
actggataag tacttcaaga accatacgtc tccggatgtg gatctcggag atataagtgg    3540
aatcaacgca agcgtagtaa acattcagaa ggagatagac cgactcaatg aggttgctaa    3600
aaacctgaac gaaagcttga tagacttgca ggagctgggt aagtacgaac agtacattaa    3660
gtggccatgg tatatctggt tgggcttcat agcaggactc atagctatcg tcatggtgac    3720
aataatgctt tgttgtatga ccagctgttg ttcttgtctg aaaggctgct gcagctgtgg    3780
cagctgttgt aaatttgacg aagatgattc cgagcctgtg cttaagggcg taaaactcca    3840
ctatacatga                                                          3850
```

METHODS FOR THE TREATMENT OF COVID-19 COMPRISING ADMINISTERING REPLICATION-DEFECTIVE ADENOVIRUSES ENCODING THE SARS-COV-2 SPIKE GLYCOPROTEIN AND MODIFIED NUCLEOCAPSID PROTEIN

This application claims priority to allowed U.S. patent application with the Ser. No. 16/883,263, filed May 26, 2020, which claims priority to U.S. provisional patent applications with the Ser. Nos. 62/988,328, filed Mar. 11, 2020; 62/991,504 filed on Mar. 18, 2020; 63/009,960 filed Apr. 14, 2020; 63/010,010, filed Apr. 14, 2020; 63/016,048, filed Apr. 27, 2020; 63/016,241, filed Apr. 27, 2020; and 63/022,146, filed May 8, 2020. Each of these applications are incorporated by reference in its entirety.

SEQUENCE LISTING

The content of the XML file of the sequence listing named 102538.0080US-CON, which is 15 KB in size was created on Mar. 29, 2023 and electronically submitted via Patent Center along with the present application. The sequence listing is incorporated by reference in its entirety.

FIELD

The present disclosure relates to composition, systems, and methods of treating subjects diagnosed or suspected to have Coronavirus Disease 2019 (COVID-19).

BACKGROUND

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

After several noteworthy coronavirus outbreaks in the recent years, including SARS and MERS, COVID-19 is yet another example of a serious infectious disease precipitated by a member of the corona virus family. While diagnostic tests have become available in relatively short time, numerous attempts to treat the disease have so far not had significant success. Most typically, patients with severe symptoms are treated to maintain respiration/blood oxygenation and supportive treatment is provided to reduce or prevent multi-organ damage or even failure. Despite such interventions, the mortality rate is significant, particularly in elderly, immune compromised individuals, and individuals with heart disease, lung disease, or diabetes.

Thus, even though various methods of addressing symptoms win patients with COVID-19 are known in the art, all or almost all of them suffer from various disadvantages. Consequently, there is a need to provide improved compositions and methods that provide therapeutic effect, that reduce or prevent viral entry into a cell, reduce direct and indirect toxicity of the virus to the patient, and that produce an immune response that is effective to clear the virus from the patient.

SUMMARY

The present disclosure is directed to various immune therapeutic compositions and methods suitable for treating and/or preventing a coronavirus disease. In one aspect, disclosed herein is a replication defective adenovirus, wherein the adenovirus comprises an E1 gene region deletion; an E2b gene region deletion; and a nucleic acid encoding a protein selected from the group consisting of coronavirus 2 (CoV2) nucleocapsid protein, CoV2 spike protein, and a combination thereof. In a second aspect of this disclosure, provided herein is a recombinant yeast comprising a nucleic acid encoding a protein selected from the group consisting of coronavirus 2 (CoV2) nucleocapsid protein, CoV2 spike protein, and a combination thereof. Preferably, the recombinant yeast is *Saccharomyces cerevisiae*.

In one embodiment of each of the above two aspects, the CoV2 nucleocapsid protein has at least 85% identity to SEQ ID NO:1. In some cases, the CoV2 nucleocapsid protein of SEQ ID NO:1 is fused to an endosomal targeting sequence (N-ETSD), wherein the N-ETSD has at least 85% identity to SEQ ID NO:2. It is further contemplated that the fusion protein contains a linker between the N-ETSD domain and the nucleocapsid protein. For example this linker may be a 16 amino acid linker having the sequence $(GGGS)_4$. The CoV2 spike protein is contemplated to have at least 85% identity to SEQ ID NO:4. The nucleic acid encoding the CoV2 spike protein has at least 99% identity to SEQ ID NO:5

In another embodiment of this disclosure, the adenoviruses and yeasts disclosed herein may further comprise a nucleic acid encoding a trafficking sequence, a co-stimulatory molecule, and/or an immune stimulatory cytokine. The co-stimulatory molecule is selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and LFA3. The immune stimulatory cytokine may be selected from the group consisting of IL-2, IL-12, IL-15, nogapendekin alfa-imbakicept, IL-21, IPS1, and LMP1.

In yet another embodiment, disclosed herein is a vaccine composition comprising the adenovirus or yeast as disclosed above, and wherein the composition is formulated for injection. The vaccine composition may be used for inducing immunity against CoV2 in a patient in need thereof, by administering to the patient the vaccine composition In another aspect, the method includes administering to the subject an immunotherapy composition comprising a recombinant entity, wherein the recombinant entity comprises a nucleic acid that encodes a nucleocapsid protein of coronavirus 2 (CoV2) and/or a spike protein of CoV2. In one embodiment, the nucleocapsid protein is ETSD.

Preferably, the nucleic acid that encodes a nucleocapsid protein of coronavirus 2 further encodes a trafficking sequence for the nucleocapsid protein. It is further contemplated that the recombinant entity may also comprise a sequence that encodes at least one of a co-stimulatory molecule and an immune stimulatory cytokine. The co-stimulatory molecule is selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and LFA3. The immune stimulatory cytokine is selected from the group consisting of IL-2, IL-12, IL-15, IL-15 super agonist (N803), IL-21, IPS1, and LMP1. In some preferred embodiments, the immune stimulatory cytokine is IL-15 super agonist N803.

The immunotherapy compositions disclosed herein to be administered subcutaneously or intravenously.

The recombinant entity contemplated herein may be a recombinant virus, such as a recombinant adenovirus. The recombinant entity may also be a recombinant yeast, such as *Saccharomyces cerevisiae*.

In some preferred embodiments, the coronavirus disease is COVID-19.

In yet another aspect of the present disclosure, disclosed herein is a vaccine formulation comprising a recombinant entity, wherein the recombinant entity comprises a nucleic acid that encodes a nucleocapsid protein of coronavirus 2 (CoV2); and/or wherein the recombinant entity encodes a spike protein of CoV2. As discussed throughout, the recombinant entity is preferably a recombinant adenovirus or *Saccharomyces cerevisiae*. The vaccine formulation may administered to a patient having a coronavirus disease for treatment and/or prevention of the coronavirus disease.

Various objects, features, aspects, and advantages will become more apparent from the following detailed description of preferred embodiments, along with the accompanying drawing in which like numerals represent like components.

BRIEF DESCRIPTION OF THE DRAWING

FIG. 6 exemplarily depicts enhanced cell surface expression of RBD with S Fusion and with S Fusion+N combination constructs compared to S-WT.

DETAILED DESCRIPTION

Figure 1:
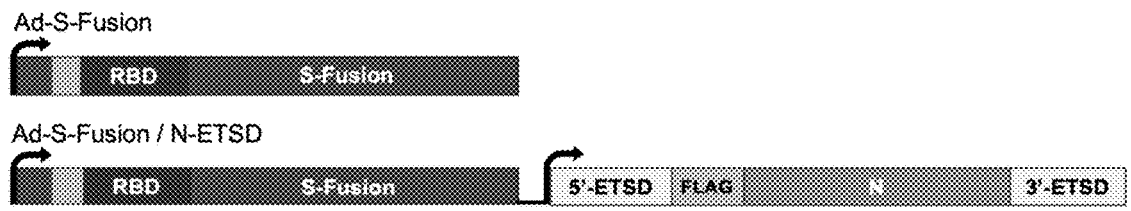
FIG. 1 exemplarily depicts vaccine constructs for Phase 1b clinical trials.
Figure 2:
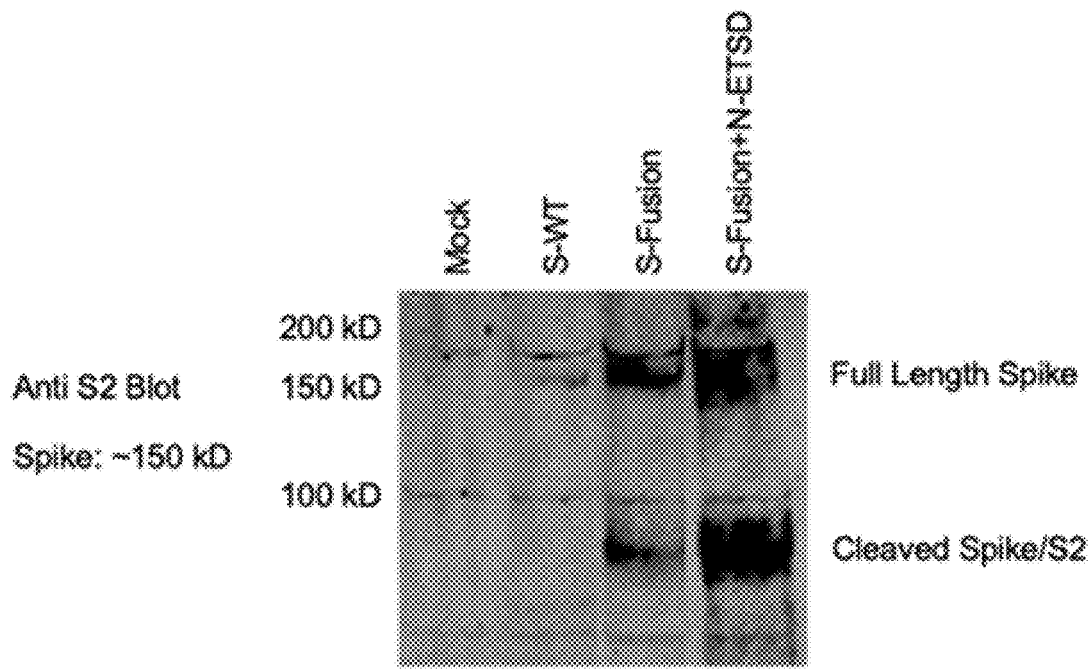
FIG. 2 exemplarily depicts in vitro Expression, Construct Expression via Western Blot, and detection of spike and nucleocapsid expression in by Western Blot.

Disclosed herein are recombinant viruses and yeasts. The viruses and yeasts disclosed herein may be useful for a variety of purposes, such as treating and/or preventing a coronavirus disease. In one aspect, disclosed herein is a replication defective adenovirus, wherein the adenovirus comprises an E1 gene region deletion; an E2b gene region deletion; and a nucleic acid encoding a protein selected from the group consisting of coronavirus 2 (CoV2) nucleocapsid protein, CoV2 spike protein, and a combination thereof.

In some embodiment, the CoV2 nucleocapsid protein comprises a sequence with at least 80% identity to SEQ ID NO:1. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

In some embodiment, the CoV2 nucleocapsid protein is fused to an endosomal targeting sequence (N-ETSD). In principle, any intracellular antigen can be driven to expression on the cell surface by tagging the antigen with ETSD as described herein. In one embodiment, the N-ETSD may comprises a sequence with at least 80% identity to SEQ ID NO:2. In other embodiments, the identity value is at least 85%. In still other embodiments, the identity value is at least 90%. In some embodiments, the identity value is at least 95%. In some embodiments, the identity value is at least 99%. In some embodiments, the identity value is 100%. It is further contemplated that the fusion protein contains a linker between the N-ETSD domain and the nucleocapsid protein. For example this linker may be a 16 amino acid linker having the sequence $(GGGS)_4$. In certain embodiments, methods are disclosed herein for enhancing the immunogenicity of an intracellular antigen, the methods comprising tagging the antigen with ETSD and expressing the tagged antigen in an antigen-presenting cell (e.g., a dendritic cell).

In some embodiments, the fusion protein comprising N-ETSD and CoV2 nucleocapsid protein may be encoded by a nucleic acid sequence having at least 80% identity to SEQ ID NO:3. In some embodiments, the identity value is at least 85%. In some embodiments, the identity value is at least 90%. In some embodiments, the identity value is at least 95%. In some embodiments, the identity value is at least 99%. In some embodiments, the identity value is 100%.

The CoV2 spike protein is contemplated to have at least 85% identity to SEQ ID NO:4. The nucleic acid encoding the CoV2 spike protein has at least 99% identity to SEQ ID NO:5

In a second aspect of this disclosure, provided herein is a recombinant yeast comprising a nucleic acid encoding a protein selected from the group consisting of coronavirus 2 (CoV2) nucleocapsid protein, CoV2 spike protein, and a combination thereof. Preferably, the recombinant yeast is *Saccharomyces cerevisiae*.

In some embodiments of this second aspect, the CoV2 nucleocapsid protein comprises a sequence with at least 80% identity to SEQ ID NO:1. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

In some embodiment of this second aspect, the CoV2 spike protein comprises a sequence with at least 80% identity to SEQ ID NO:4. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

In some embodiments, the nucleic acid encoding the CoV2 spike protein comprises a sequence with at least 80% identity to SEQ ID NO:5. In other embodiments, the identity value is at least 85%. In still other embodiments, the identity value is at least 90%. In some embodiments, the identity value is at least 95%. In some embodiments, the identity value is at least 99%. In some embodiments, the identity value is 100%.

The adenoviruses and yeasts disclosed herein may further comprise a nucleic acid encoding a trafficking sequence, a co-stimulatory molecule, and/or an immune stimulatory cytokine. The co-stimulatory molecule is selected from the group consisting of CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and LFA3. The immune stimulatory cytokine may be selected from the group consisting of IL-2, IL-12, IL-15, nogapendekin alfa-imbakicept, IL-21, IPS1, and LMP1. Additionally or alternatively, the vaccines disclosed herein may also encode SARS-CoV-2 M protein, with or without an ETSD tag.

In yet another embodiment, disclosed herein is a vaccine composition comprising the adenovirus or yeast as disclosed above, and wherein the composition is formulated for injection. The vaccine composition may be used for inducing immunity against CoV2 in a patient in need thereof, by administering to the patient the vaccine composition Also disclosed herein are methods for preventing and/or treating coronavirus diseases, and especially COVID-19. Preferably, the method includes using a viral or yeast vector that encodes the nucleocapsid protein and/or spike protein of the coronavirus in an immunogenic composition that is administered to a subject individual. The virus and/or yeast vaccine, thus administered, would infect the individual with CoV2 nucleocapsid or spike protein. With that in place, the individual would have an immune response against it, and be vaccinated. Notably, as the nucleocapsid protein and the spike protein are relatively conserved polypeptides, immune responses can be elicited for a variety of members of the coronavirus family.

Where the recombinant vector is an adenovirus, the adenoviral vector may be modified to encode the nucleocapsid protein, and/or the spike protein. Similarly, in case of yeast, the yeast vector may also be modified to encode the nucleocapsid protein, and/or the spike protein. Positive responses were obtained on cell mediated immunity upon administration of immunogenic compositions comprising the viral and/or yeast vectors in patients in need thereof. Thus, in one embodiment, the present disclosure envision creating the coronaviral spikes to be expressed on the yeast surface. So, in this embodiment, the yeast is acting as an avatar coronavirus to stimulate the B cells. The stimulation of the B cells then results in humoral immunity.

Coronaviruses

Coronaviruses are found in avian and mammalian species. They resemble each other in morphology and chemical structure: for example, the coronaviruses of humans and cattle are antigenically related. There is no evidence, however, that human coronaviruses can be transmitted by animals. In animals, various coronaviruses invade many different tissues and cause a variety of diseases in humans. One such disease was Severe acute respiratory syndrome (SARS) coronavirus disease that spread to several countries in Asia, Europe and North America in late 2002/early 2003. Another such disease is the novel Coronavirus Disease of 2019 (COVID 19) that has spread to several countries in the world.

COVID 19 usually begins with a fever greater than 38° C. Initial symptoms can also include cough, sore throat, malaise and mild respiratory symptoms. Within two days to a week, patients may have trouble breathing. Patients in more advanced stages of COVID 19 develop either pneumonia or respiratory distress syndrome. Public health interventions, such as surveillance, travel restrictions and quarantines, are being used to contain the spread of COVID 19. It is unknown, however, whether these draconian containment measures can be sustained with each appearance of the COVID 19 in humans. Furthermore, the potential of this new and sometimes lethal CoV as a bio-terrorism threat is obvious.

Coronavirus virions are spherical to pleomorphic enveloped particles. The envelope is studded with projecting glycoproteins, and surrounds a core consisting of matrix protein enclosed within which is a single strand of positive-sense RNA (Mr $6\times10^6$) associated with nucleocapsid protein. In that regard, it should be noted that the terms "nucleocapsid protein," "nucleoprotein," and "nucleocapsid" are used interchangeably throughout this disclosure. The coronavirus nucleocapsid (N) is a structural protein found in all coronaviruses, including COVID 19. The nucleocapsid protein forms complexes with genomic RNA, interacts with the viral membrane protein during virion assembly and plays a critical role in enhancing the efficiency of virus transcription and assembly.

Another protein found throughout all coronavirus virions is the viral spike(S) protein. Coronaviruses are large positive-stranded RNA viruses typically with a broad host range. Like other enveloped viruses, CoV enter target cells by fusion between the viral and cellular membranes, and that process is mediated by the viral spike (S) protein.

The methods and compositions disclosed herein target the nucleoprotein and the spike protein that is conserved in all types of coronaviruses. In one embodiment, the present disclosure provides a vaccine formulation comprising a recombinant entity, wherein the recombinant entity comprises a nucleic acid that encodes a nucleocapsid protein of coronavirus 2 (CoV2); and/or wherein the recombinant entity encodes a spike protein of CoV2. The vaccine formulation may be useful for treating a disease, such as a coronavirus mediated disease or infection. Thus, in another embodiment, disclosed is a method for treating a coronavirus disease, in a patient in need thereof, comprising: administering to the subject an immunotherapy composition comprising a recombinant entity, wherein the recombinant entity comprises a nucleic acid that encodes a nucleocapsid protein of coronavirus 2 (CoV2). The coronavirus contemplated herein may be coronavirus disease 2019 (COVID-19) and/or severe acute respiratory syndrome coronavirus 2 (SARS-CoV2)

The instant disclosure also provides a method for treating coronavirus disease 2019 (COVID-19) and/or severe acute respiratory syndrome coronavirus 2 (SARS-CoV2), in a patient in need thereof, comprising: administering to the subject a first immunotherapy composition comprising a recombinant virus, wherein the recombinant virus comprises a nucleic acid that encodes a nucleocapsid protein of coronavirus 2 (CoV2), administering to the subject a second immunotherapy composition comprising a recombinant yeast, wherein the recombinant yeast comprises a nucleic acid that encodes a spike protein of CoV2. The first and second immunotherapy compositions may be administered concurrently or sequentially to the patient.

Viewed form a different perspective, contemplated herein is a viral vector (e.g., recombinant adenovirus genome, optionally with a deleted or non-functional E2b gene) that comprises a nucleic acid that encodes (a) at least a nucleocapsid protein; and (b) at least one spike protein. The viral vector may further comprise co-stimulatory molecule. Most typically, the nucleic acid will further include a trafficking signal to direct a peptide product encoded by the nucleic acid to the cytoplasm, the endosomal compartment, or the lysosomal compartment, and the peptide product will further comprise a sequence portion that enhances intracellular turnover of the peptide product.

Recombinant Viruses

With respect to recombinant viruses it is contemplated that all known manners of making recombinant viruses are deemed suitable for use herein, however, especially preferred viruses are those already established in therapy, including adenoviruses, adeno-associated viruses, alphaviruses, herpes viruses, lentiviruses, etc. Among other appropriate choices, adenoviruses are particularly preferred.

Moreover, it is further generally preferred that the virus is a replication deficient and non-immunogenic virus. For example, suitable viruses include genetically modified alphaviruses, adenoviruses, adeno-associated viruses, herpes viruses, lentiviruses, etc. However, adenoviruses are particularly preferred. For example, genetically modified replication defective adenoviruses are preferred that are suitable not only for multiple vaccinations but also vaccinations in individuals with preexisting immunity to the adenovirus (see e.g., WO 2009/006479 and WO 2014/031178, which are incorporated by reference in its entirety). In some embodiments, the replication defective adenovirus vector comprises a replication defective adenovirus 5 vector. In some embodiments, the replication defective adenovirus vector comprises a deletion in the E2b region. In some embodiments, the replication defective adenovirus vector further comprises a deletion in the E1 region. In that regard, it should be noted that deletion of the E2b gene and other late proteins in the genetically modified replication defective adenovirus to reduce immunogenicity. Moreover, due to these specific deletions, such genetically modified viruses were replication deficient and allowed for relatively large recombinant cargo.

For example, WO 2014/031178 describes the use of such genetically modified viruses to express CEA (colorectal embryonic antigen) to provide an immune reaction against colon cancer. Moreover, relatively high titers of recombinant viruses can be achieved using genetically modified human 293 cells as has been reported (e.g., *J Virol.* 1998 February; 72(2): 926-933).

E1-deleted adenovirus vectors Ad5 [E1-] are constructed such that a trans gene replaces only the E1 region of genes. Typically, about 90% of the wild-type Ad5 genome is retained in the vector. Ad5 [E1-] vectors have a decreased ability to replicate and cannot produce infectious virus after infection of cells not expressing the Ad5 E1 genes. The recombinant Ad5 [E1-] vectors are propagated in human cells allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus sc, im, or iv. Additionally, Ad5 vectors do not integrate; their genomes remain episomal. Generally, for vectors that do not integrate into the host genome, the risk for insertional mutagenesis and/or germ-line transmission is extremely low if at all. Conventional Ad5 [E1-] vectors have a carrying capacity that approaches 7 kb.

One obstacle to the use of first generation (E1-deleted) Ad5-based vectors is the high frequency of pre-existing anti-adeno virus type 5 neutralizing antibodies. Attempts to overcome this immunity is described in WO 2014/031178, which is incorporated by reference herein. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. E2b deleted adenovirus vectors provide an improved Ad-based vector that is safer, more effective, and more versatile than First Generation adenovirus vectors.

In a further embodiment, the adenovirus vectors contemplated for use in the present disclosure include adenovirus vectors that have a deletion in the E2b region of the Ad genome and, optionally, deletions in the E1, E3 and, also optionally, partial or complete removal of the E4 regions. In a further embodiment, the adenovirus vectors for use herein have the E1 and/or the preterminal protein functions of the E2b region deleted. In some cases, such vectors have no other deletions. In another embodiment, the adenovirus vectors for use herein have the E1, DNA polymerase and/or the preterminal protein functions deleted.

The term "E2b deleted", as used herein, refers to a specific DNA sequence that is mutated in such a way so as to prevent expression and/or function of at least one E2b gene product. Thus, in certain embodiments, "E2b deleted" is used in relation to a specific DNA sequence that is deleted (removed) from the Ad genome. E2b deleted or "containing a deletion within the E2b region" refers to a deletion of at least one base pair within the E2b region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E2b region of the Ad genome. An E2b deletion may be a deletion that prevents expression and/or function of at least one E2b gene product and therefore, encompasses deletions within exons of encoding portions of E2b-specific proteins as well as deletions within promoter and leader sequences. In certain embodiments, an E2b deletion is a deletion that prevents expression and/or function of one or both of the DNA polymerase and the preterminal protein of the E2b region. In a further embodiment, "E2b deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

As noted before, the desired nucleic acid sequences (for expression from virus infected cells) are under the control of appropriate regulatory elements well known in the art. In view of the above, it should be appreciated that compositions and methods presented are not only suitable for directing virally expressed antigens specifically to one or another (or both) MHC systems, but will also provide increased stimulatory effect on the CD8+ and/or CD4+ cells via inclusion of various co-stimulatory molecules (e.g., ICAM-1 (CD54), ICOS-L, LFA-3 (CD58), and at least one of B7.1 (CD80) and B7.2 (CD86)), and via secretion or membrane bound presentation of checkpoint inhibitors.

With respect to viral expression and vaccination systems it is contemplated that all therapeutic recombinant viral expression systems are deemed suitable for use herein so long as such viruses are capable to lead to expression of the recombinant payload in an infected cell.

Regardless of the type of recombinant virus it is contemplated that the virus may be used to infect patient (or non-patient) cells ex vivo or in vivo. For example, the virus may be injected subcutaneously or intravenously, or may be administered intranasaly or via inhalation to so infect the patient's cells, and especially antigen presenting cells. Alternatively, immune competent cells (e.g., NK cells, T cells, macrophages, dendritic cells, etc.) of the patient (or from an allogeneic source) may be infected in vitro and then transfused to the patient. Alternatively, immune therapy need not rely on a virus but may be effected with nucleic acid transfection or vaccination using RNA or DNA, or other recombinant vector that leads to the expression of the neoepitopes (e.g., as single peptides, tandem mini-gene, etc.) in desired cells, and especially immune competent cells.

As noted above, the desired nucleic acid sequences (for expression from virus infected cells) are under the control of appropriate regulatory elements well known in the art. For example, suitable promoter elements include constitutive strong promoters (e.g., SV40, CMV, UBC, EF1A, PGK, CAGG promoter), but inducible promoters are also deemed suitable for use herein, particularly where induction conditions are typical for a tumor microenvironment. For example, inducible promoters include those sensitive to hypoxia and promoters that are sensitive to TGF-β or IL-8 (e.g., via TRAF, JNK, Erk, or other responsive elements promoter). In other examples, suitable inducible promoters include the tetracycline-inducible promoter, the myxovirus resistance 1 (Mx1) promoter, etc.

The replication defective adenovirus comprising an E1 gene region deletion, an E2b gene region deletion, and a nucleic acid encoding a coronavirus 2 (CoV2) nucleocapsid protein and/or a CoV2 spike protein, as disclosed herein may be administered to a patient in need for inducing immunity against CoV2. Routes and frequency of administration of the therapeutic compositions described herein, as well as dosage, may vary from individual to individual, and the severity of the disease, and may be readily established using standard techniques. In some embodiments, the administration comprises delivering $4.8\text{-}5.2\times10^{11}$ replication defective adenovirus particles, or $4.9\text{-}5.1\times10^{11}$ replication defective adenovirus particles, or $4.95\text{-}5.05\times10^{11}$ replication defective adenovirus particles, or $4.99\text{-}5.01\times10^{11}$ replication defective adenovirus particles.

The administration of the virus particles can be through a variety of suitable paths for delivery. One preferred route contemplated herein is by injection, such as intracutaneous injection, intramuscular injection, intravenous injection or subcutaneous injection. In some embodiments, a subcutaneous delivery may be preferred.

Recombinant Yeasts

With respect to yeast expression and vaccination systems, it is contemplated that all known yeast strains are deemed suitable for use herein. However, it is preferred that the yeast is a recombinant *Saccharomyces* strain that is genetically modified with a nucleic acid construct encoding a protein selected from the group consisting of coronavirus 2 (CoV2) nucleocapsid protein, CoV2 spike protein, and a combination thereof, to thereby initiate an immune response against the CoV2 viral disease. In one aspect of any of the embodiments of the disclosure described above or elsewhere herein, the yeast vehicle is a whole yeast. The whole yeast, in one aspect is killed. In one aspect, the whole yeast is heat-inactivated. In one preferred embodiment, the yeast is a whole, heat-inactivated yeast from *Saccharomyces cerevisiae.*

The use of a yeast based therapeutic compositions are disclosed in the art. For example, WO 2012/109404 discloses yeast compositions for treatment of chronic hepatitis b infections.

It is noted that any yeast strain can be used to produce a yeast vehicle of the present disclosure. Yeasts are unicellular microorganisms that belong to one of three classes: Ascomycetes, Basidiomycetes and Fungi Imperfecti. One consideration for the selection of a type of yeast for use as an immune modulator is the pathogenicity of the yeast. In preferred embodiments, the yeast is a non-pathogenic strain such as *Saccharomyces cerevisiae* as non-pathogenic yeast strains minimize any adverse effects to the individual to whom the yeast vehicle is administered. However, pathogenic yeast may also be used if the pathogenicity of the yeast can be negated using pharmaceutical intervention.

For example, suitable genera of yeast strains include *Saccharomyces, Candida, Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in a preferred aspect, *Saccharomyces* is used. Species of yeast strains that may be used include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica.*

It should further be appreciated that a number of these species include a variety of subspecies, types, subtypes, etc. that are intended to be included within the aforementioned species. In one aspect, yeast species used in the instant disclosure include *S. cerevisiae, C. albicans, H. polymorpha, P. pastoris* and *S. pombe. S. cerevisiae* is useful due to it being relatively easy to manipulate and being "Generally Recognized As Safe" or "GRAS" for use as food additives (GRAS, FDA proposed Rule 62FR18938, Apr. 17, 1997). Therefore, particularly contemplated herein is a yeast strain that is capable of replicating plasmids to a particularly high copy number, such as a *S. cerevisiae* cir strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used, including those that exhibit reduced post-translational modifications of expressed target antigens or other proteins, such as mutations in the enzymes that extend N-linked glycosylation.

Expression of contemplated peptides/proteins in yeast can be accomplished using techniques known to those skilled in the art. Most typically, a nucleic acid molecule encoding at least one protein is inserted into an expression vector such manner that the nucleic acid molecule is operatively linked to a transcription control sequence to be capable of effecting either constitutive or regulated expression of the nucleic acid molecule when transformed into a host yeast cell. As will be readily appreciated, nucleic acid molecules encoding one or more proteins can be on one or more expression vectors operatively linked to one or more expression control sequences. Particularly important expression control sequences are those which control transcription initiation, such as promoter and upstream activation sequences.

Any suitable yeast promoter can be used in the methods and compositions of the present disclosure and a variety of such promoters are known to those skilled in the art and have generally be discussed above. Promoters for expression in *Saccharomyces cerevisiae* include promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SEC7) and acid phosphatase (PHO5), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the alpha-factor, GAPDH, and CYC1 genes. Transcription control sequences to express genes in methyltrophic yeast include the transcription control regions of the genes encoding alcohol oxidase and formate dehydrogenase.

Likewise, transfection of a nucleic acid molecule into a yeast cell according to the present disclosure can be accomplished by any method by which a nucleic acid molecule administered into the cell and includes diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins. Further exemplary yeast expression systems, methods, and conditions suitable for use herein are described in US20100196411A1, US2017/0246276, or US 2017/0224794, and US 2012/0107347.

So produced recombinant viruses and yeasts may then be individually or in combination used as a therapeutic vaccine in a pharmaceutical composition, typically formulated as a sterile injectable composition with a virus of between $10^4$-$10^{13}$ virus or yeast particles per dosage unit, or more preferably between $10^9$-$10^{12}$ virus or yeast particles per dosage unit. Alternatively, virus or yeast may be employed to infect patient cells ex vivo and the so infected cells are then transfused to the patient. However, alternative formulations are also deemed suitable for use herein, and all known routes and modes of administration are contemplated herein.

Second Generation hAd5 [E1-, E2b-, E3-] Based Vaccines Disclosed Herein Overcome Pre-Existing Anti-Ad5 Immunity To avoid the Ad immunization barrier and circumvent the adverse conditions for first generation Ad5 [E1-E3-] vectors, an advanced 2nd generation human adenoviral (hAd5) vector was constructed having two (2) additional deletions in the E2b region, removing the DNA polymerase and the preterminal protein genes [E1-, E2b-, E3-]. (Former names of our adenovirus vector were Ad5, ETBX in literature)

E2b-deleted hAd5 vectors have up to a 12-14 kb gene-carrying capacity as compared to the 7-kb capacity of first generation Ad5 [E1-] vectors, providing space for multiple genes if needed. hAd5 [E1-, E2b-, E3-] based recombinant vectors are produced using the human E.C7 cell line. Deletion of the E2b region also confers advantageous immune properties on these novel Ad vectors, eliciting potent immune responses to specific, non-viral antigens while minimizing the immune responses to Ad viral proteins.

hAd5 [E1-, E2b-, E3-] vectors induce a potent cell mediated immune (CMI) response, as well as Abs against the vectored antigens even in the presence of Ad immunity. hAd5 [E1-, E2b-, E3-] vectors also have reduced adverse reactions as compared to Ad5 [E1-] vectors, in particular the appearance of hepatotoxicity and tissue damage. In one embodiment, the reduced inflammatory response against hAd5 [E1-, E2b-, E3-] vector viral proteins and the resulting evasion of pre-existing Ad immunity increases the capability for the hAd5 [E1-, E2b-, E3-] vectors to infect dendritic cells (DC), resulting in greater immunization of the vaccine. In addition, increased infection of other cell types provides high levels of antigen presentation needed for a potent CD8+ and CD4+ T cell responses, leading to memory T cell development. In one embodiment, hAd5 [E1-, E2b-, E3-] vectors are superior to Ad5 [E1-] vectors in immunogenicity and safety and will be the best platform to develop a COVID-19 vaccine in a rapid and efficient manner. In one embodiment, a prophylactic vaccine is tested against COVID-19 by taking advantage of this new hAd5 vector system that overcomes barriers found with other Ad5 systems and permits the immunization of people who have previously been exposed to Ad5.

Track Record of Rapid Vaccine Development Utilizing Second Generation Human (hAd5) Adenovirus Platform During Pandemic Treats: H1N1 Experience in 2009

To address emerging pathogen threats, especially in times of pandemic, it is critical that modernized vaccine technologies be deployed. These technologies will utilize the power of genomic sequencing, rapid transfection in well-established vaccine vectors to rapidly identify constructs with high immunogenicity.

Figure 3:
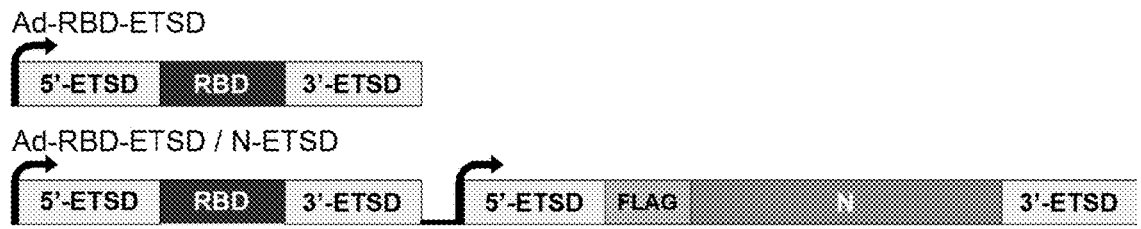
FIG. 3 exemplarily depicts COVID-19 vaccine constructs.

Vaccines against emerging pathogens such as the 2009 H1N1 pandemic virus can benefit from current technologies such as rapid genomic sequencing to construct the most biologically relevant vaccine. A novel platform (hAd5 [E1-, E2b-, E3-]) has been utilized to induce immune responses to various antigenic targets. This vector platform expressed hemagglutinin (HA) and neuraminidase (NA) genes from 2009 H1N1 pandemic viruses. Inserts were consensuses sequences designed from viral isolate sequences and the vaccine was rapidly constructed and produced. Vaccination induced H1N1 immune responses in mice, which afforded protection from lethal virus challenge. In ferrets, vaccination protected from disease development and significantly reduced viral titers in nasal washes. H1N1 cell mediated immunity as well as antibody induction correlated with the prevention of disease symptoms and reduction of virus replication. The hAd5 [E1-, E2b-, E3-] has thus demonstrated the capability for the rapid development of effective vaccines against infectious diseases.

hAd5 Vaccine Constructs and Results

Disclosed herein are constructs that have been constructed and tested, a hAd5-COVID-19 vaccine construct E1-, E2b-, E3-hAd5 vector with SARS-CoV-2 (S/N) protein insert (FIG. 1). This construct has been tested in preclinical experiments, including in vitro expression (FIG. 2) and small animal immunogenicity.

In addition, ImmunityBio has developed multiple COVID-19 constructs including RBD-alone, S1-alone, S1-fusion proteins, and combinations of RBD, S1 and S1 fusions with N. Preliminary in-vitro studies demonstrate that these constructs (FIG. 3) recognize convalescent serum antibodies and could serve as alternative vaccines following analysis of the two (2) constructs above (FIG. 1) which is intended to initiate in our first in human Phase 1b study.

Rationale for Inclusion of Nucleocapsid (N) in hAd5 Constructs for COVID-19

The nucleocapsid (N) protein of SARS-CoV-2 is highly conserved and highly expressed. Previous research with the related coronavirus that causes SARS demonstrated that N protein is immunogenic (Gupta, 2006), when integrated with intracellular trafficking constructs. To date, vaccine strategies in development all involve developing immunogenicity against spike (S) protein. However, very recent evidence in patients who recovered from COVID-19 demonstrates Th1 immunity generated against the nucleocapsid (N) (Grifoni, 2020). A second report by Grifoni et al. further confirmed that in the predictive bioinformatics model, T and B cell epitopes were highest for both spike glycoprotein and nucleoprotein (Grifoni, 2020). The present disclosure confirms the potential that combining S with N, that long-term cell-mediated immunity with a Th1 phenotype can be induced. The potential exists for this combination vaccine to serve as a long-term "universal" COVID-19 vaccine in light of mutations undergoing in S and the finding that the structural N protein is highly conserved in the coronavirus family. The clinical trial is designed to compare S alone versus S+N, to demonstrate safety and to better inform the immunogenicity of S and S+N. A single construct having S & N would be selected to induce potent humoral and cell mediated immunity.

Immunogenicity Studies (Small Animal Model)

Homologous prime-boost immunogenicity in BALB-c mice. Mice have been treated with 1, 2 or 3 doses of the hAd5 COVID-19 vaccine and serum and splenocyte samples are being tested for SARS-CoV-2 antigen-specific immune responses. Serum is tested for anti-spike and anti-nucleocapsid antibody responses by ELISA. Splenocytes is tested for spike- and nucleocapsid-specific cell mediated immune responses by ELISPOT and intracellular cytokine simulation assays.

The results show promising immunogenic activity. In one embodiment, hAd5 [E1-, E2b-, E3-] N-ETSD, a vaccine containing SARS-CoV-2 nucleocapsid plus an enhanced T cell stimulation domain (ETSD), alters T cell responses to nucleocapsid. Mice were immunized subcutaneously (SC) with a dose of 1010 VP twice at 7-day intervals. Blood was collected at several time points and spleen was collected upon sacrifice in order to perform immunogenicity experiments. Splenocytes were isolated and tested for cell mediated immune (CMI) responses. The results showed that SARS-CoV-2 nucleocapsid antigen specific CMI responses were detected by ELISpot and flow cytometry analyses in the spleens of all the mice immunized with hAd5 [E1-, E2b-, E3-] N-ETSD vaccine but not vector control (hAd5 [E1-, E2b-, E3-] null) immunized mice.

Figure 4:
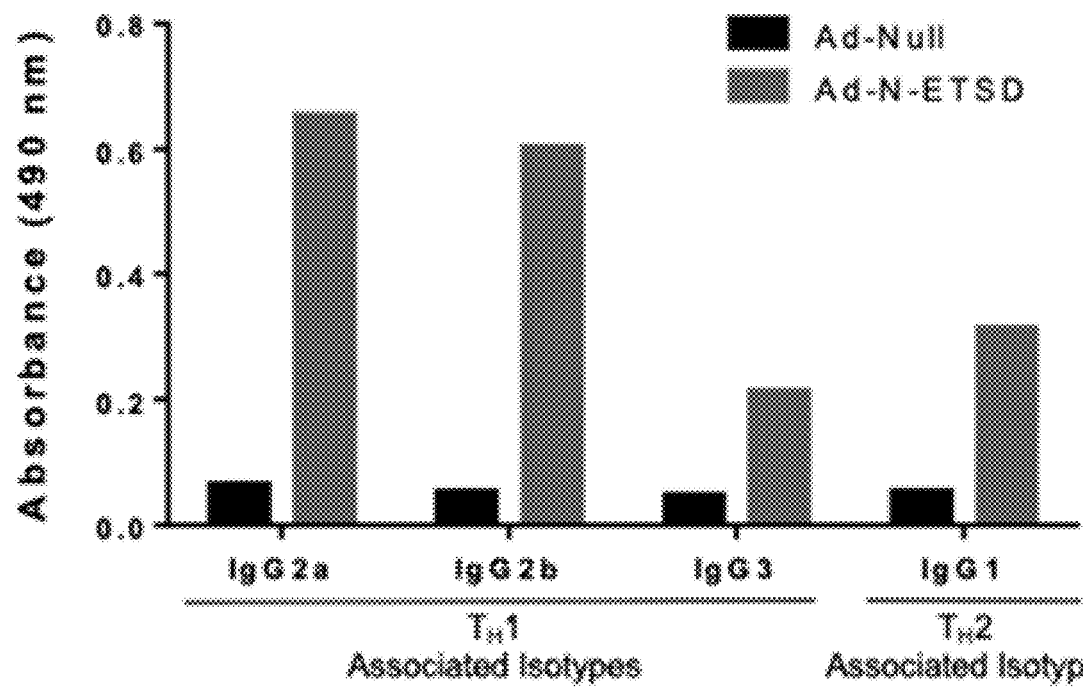
FIG. 4 exemplarily depicts antibody response to N with a Th1 phenotype. Humoral Immune Responses TH1 vs TH2 associated isotype analysis is shown.
Figure 5:
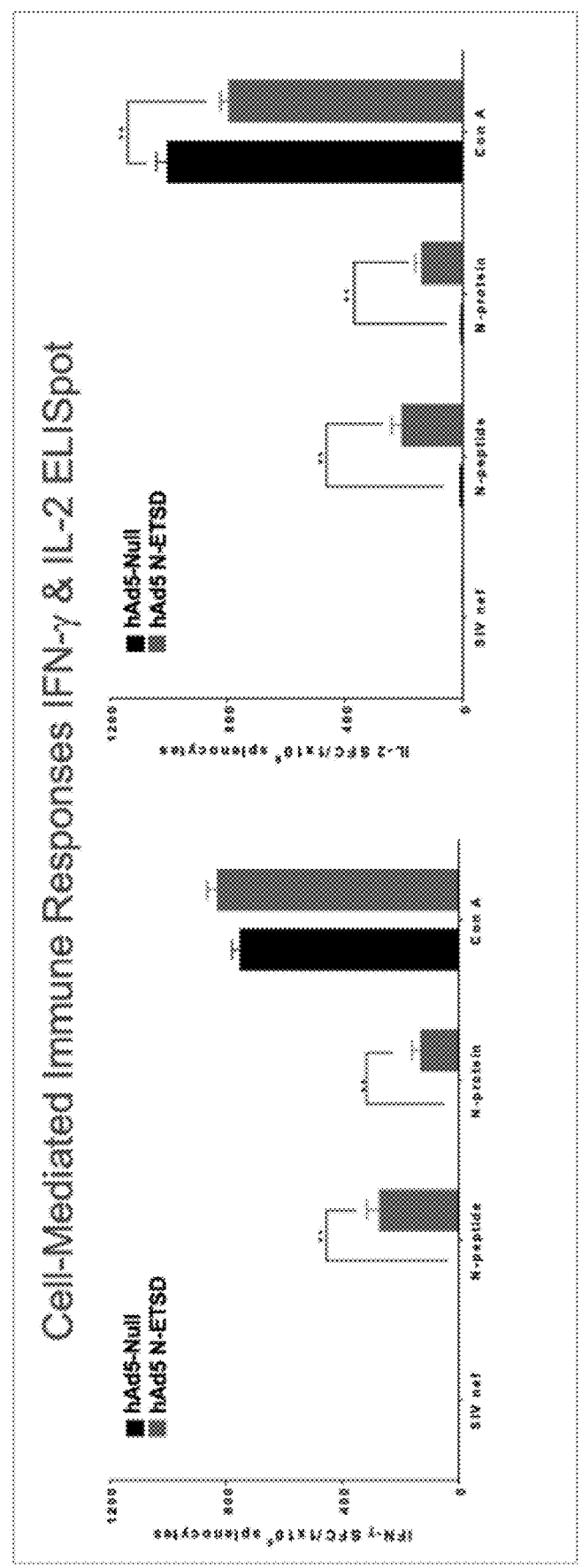
FIG. 5 exemplarily depicts cell mediated immunity (CMI) response to N focus phenotype—IFN-γ and IL-2 ELISpot.

In addition, antibody responses were detected in all the mice immunized with hAd5 [E1-, E2b-, E3-]-N-ETSD vaccine but not vector control (Ad5 [E1-, E2b-, E3-]-null) immunized mice (FIG. 4 & FIG. 5). Additional studies to confirm and extend these results are ongoing.

Enhanced RBD Cell Surface Expression

Figure 6:
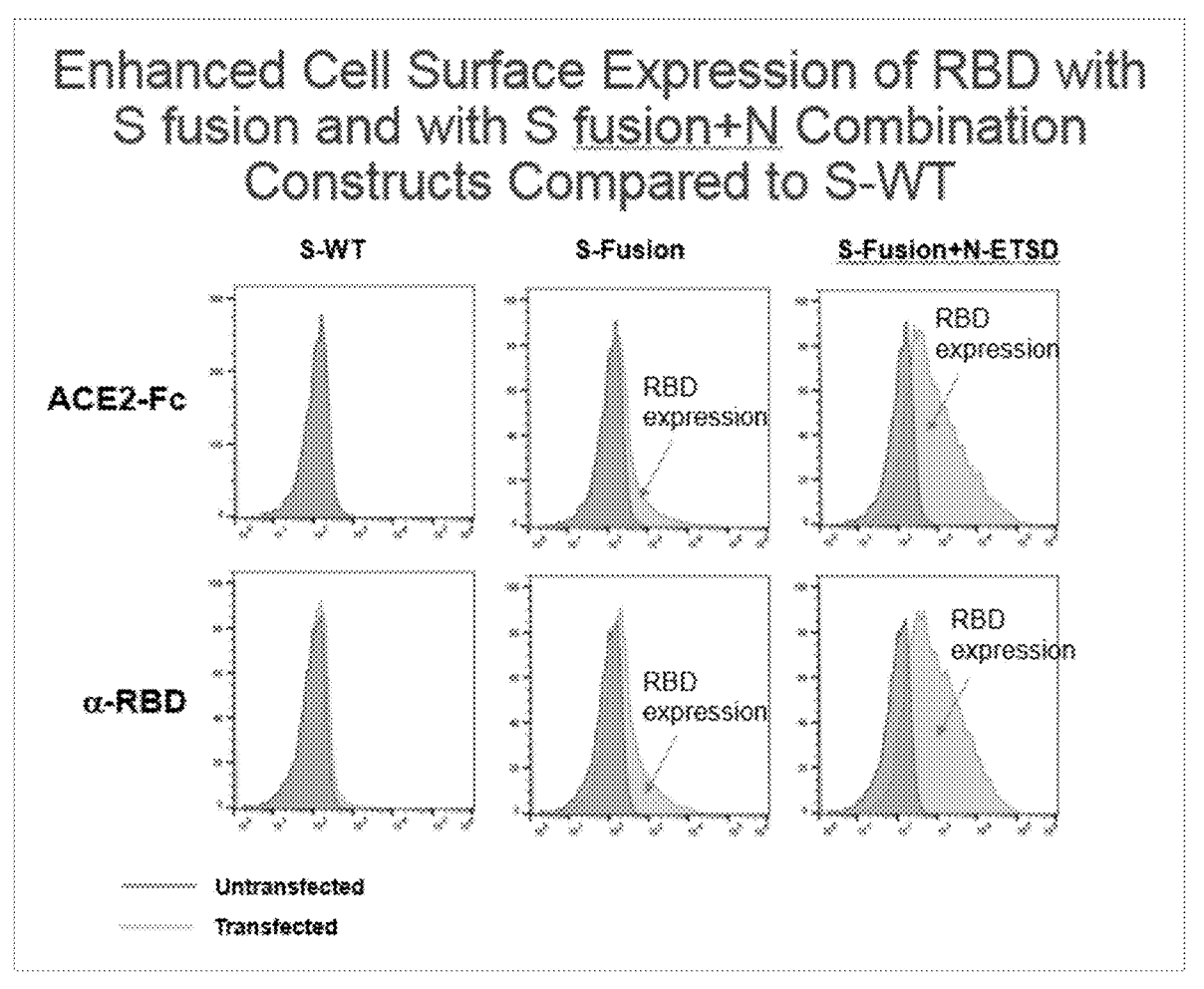

Further evidence of the potential enhancing immunogenicity value of N when combined with S was the surprising finding of enhanced surface expression of the RBD protein in 293 cells transfected with the N-ETSD+S construct as seen in FIG. 6. Expression and presentation of RBD appears to be highly important as evidenced by the recent report by Robbiani et al who showed that rare but recurring RBD-specific antibodies with potent antiviral activity were found in all individuals tested who had recovered from COVID-19 infections (Robbiani 2020).

Figure 7:
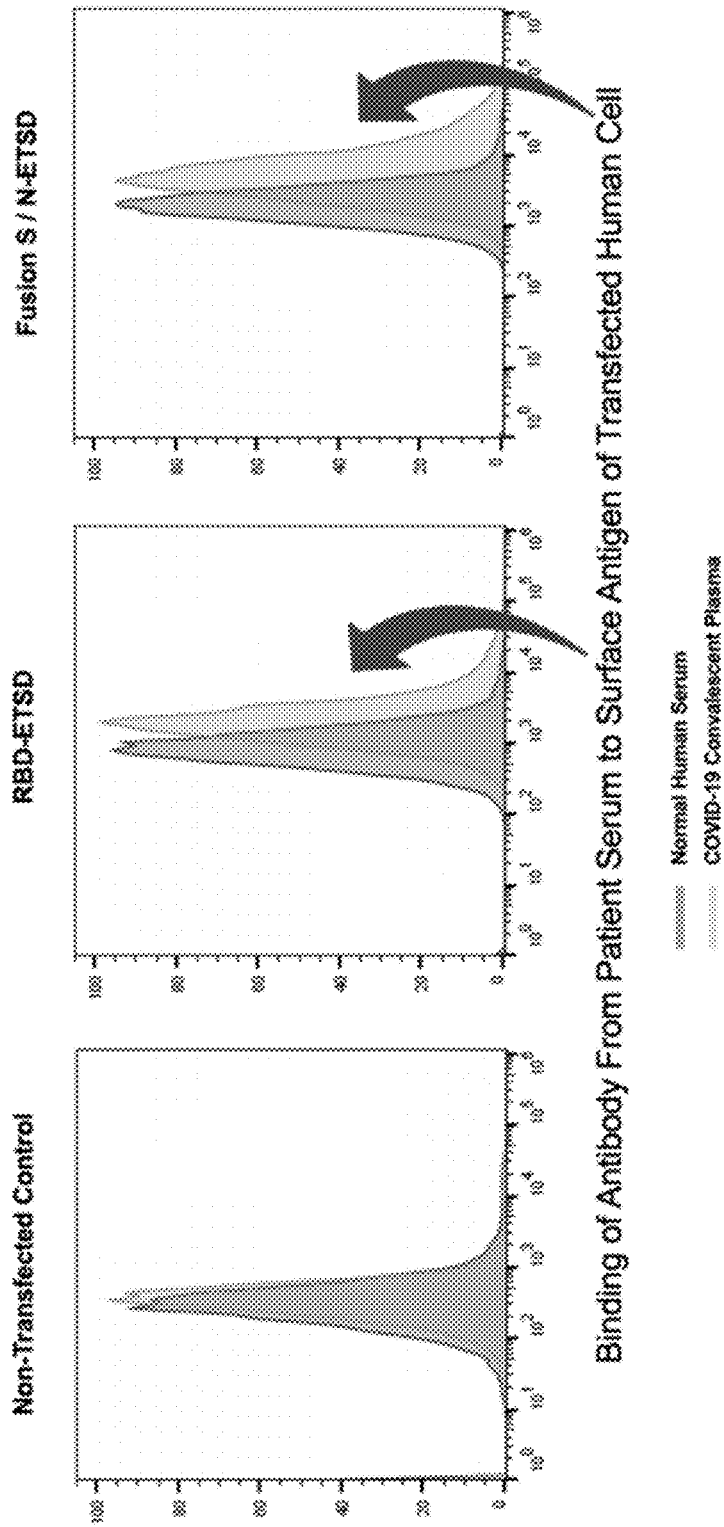
FIG. 7 exemplarily depicts that recovered COVID-19 patient plasma recognizes antigens expressed by NANT's RBD-ETSD and NANT fusion S/N-ETSD constructs.

This finding of enhanced expression of RBD when N is combined with S-Fusion was corroborated in studies using plasma from a patient recovered from COVID-19 infection (FIG. 7). The alternative construct of RBD-ETSD could serve as alternative vaccines following analysis of the two (2) constructs above (FIG. 1) which is intended to initiate in human Phase Ib studies.

In summary, on the basis of enhanced expression and exposure of the RBD protein with S Fusion and S Fusion+N construct, both were tested in the hAd5 vector. Furthermore, on the basis of recent clinical data from patients recovered from COVID-19, as well as the corroborating preclinical data that the N construct induces long lasting $CD4^+$ and Th1 cell-mediated immunity, this combination of S Fusion+N construct could provide long-lasting immunity beyond short term neutralizing antibodies.

Immunogenicity Testing of Candidate COVID-19 Vaccine Constructs

Two (2) Adenovirus-based COVID-19 vaccine constructs will be tested in preclinical experiments, including in vitro expression; small animal immunogenicity, and non-human primate immunogenicity and efficacy.

Constructs description: ImmunityBio has generated two (2) second generation hAd5-based COVID-19 vaccine constructs for preclinical testing and clinical evaluation. First is a hAd5 vector with SARS-CoV-2 with spike protein insert (see FIG. 1). Second is E1-, E2b-, E3-hAd5 vector with SARS-CoV-2 wild type spike protein (S) insert and Nucleocapsid protein (N) insert containing an Endosomal-targeting domain sequence (ETSD) in the same vector backbone.

Immunogenicity Studies: Homologous prime-boost immunogenicity in mice was examined by treating Mice with 1, 2 or 3 doses of the ImmunityBio adenovirus vaccine candidates listed in FIG. 1 and serum and splenocyte samples will be tested for SARS-CoV-2 antigen-specific immune responses. Serum is being tested for anti-spike and anti-nucleocapsid antibody responses by ELISA. Splenocytes will be tested for spike- and nucleocapsid-specific cell mediated immune responses by ELISPOT and intracellular cytokine simulation assays. Data from these studies are disclosed throughout this disclosure.

SARS-CoV-2 Virus Neutralization Studies: Serum from the mice immunized during the course of the immunogenicity studies described above is used will be sent to a third-party subcontractor for SARS-CoV-2 neutralization studies to be performed in their ABSL-3 facility. Serum will be tested for COVID 19 virus neutralizing activity by mixing various dilutions of serum with COVID 19 virus, incubating the mixture, and then exposing the mixture to Vero cells to detect cytopathic effect (CPE). The last dilution that prevents CPE will be considered the endpoint neutralizing titer.

Immunogenicity and Efficacy Evaluation in Non-Human Primates (third-party subcontractor): Rhesus macaques will be treated with three doses of the ImmunityBio adenovirus vaccine candidates listed in FIG. 1. SARS-CoV-2 antigen-specific immune responses will be monitored in serum and PBMCs by ELISA, ELISPOT and ICS throughout the course of the therapy. Four weeks after the final vaccination, animals will be challenged with SARS-CoV-2 and monitored for disease hallmarks and virus shedding.

Phase Ib Clinical trial: ImmunityBio has submitted an IND for Phase Ib clinical trial testing of hAd5 [E1-, E2b-, E3-] CoV-2 vaccine.

Study Design: This is a Phase 1b open-label study in adult healthy subjects. This clinical trial is designed to assess the safety, reactogenicity, and immunogenicity of the hAd5-COVID-19-S and hAd5-COVID-19-S/N vaccines. The hAd5-COVID-19-S and hAd5-COVID-19-S/N vaccines are hAd5 [E1-, E2b-, E3-] vector-based targeting vaccines encoding the SARS-CoV-2 Spike (S) protein alone or together with the SARS-CoV-2 nucleocapsid (N) protein. The hAd5 [E1-, E2b-, E3-] vector is the platform technology for targeted vaccines that has demonstrated safety in over 125 patients with cancer to date at doses as high as $5\times1011$ virus particles per dose. Co-administration of three different hAd5 [E1-, E2b-, E3-] vector-based vaccines on the same day at $5\times1011$ virus particles per dose each ($1.5\times1012$ total virus particles) has also been demonstrated to be safe.

COVID-19 infection causes significant morbidity and mortality in a worldwide population. The hAd5-COVID-19-S and hAd5-COVID-19-S/N vaccines are designed to induce both a humoral and cellular response even in individuals with pre-existing adenoviral immunity. Thus, the potential exists for the hAd5-COVID-19-S and hAd5-COVID-19-S/N to induce anti-COVID-19 immunity and prevent or lessen the health impact of COVID-19 infection in healthy subjects.

Phase 1b Safety Analysis: In the initial safety analysis of phase 1b, a total of 40 healthy subjects will be divided into 4 dosing cohorts (cohorts 1A, 1B, 2A, 2B; n=10 for each cohort):
Cohort 1A—hAd5-COVID-19-S at $5\times1010$ viral particles (VP) per dose (n=10),
Cohort 1B—hAd5-COVID-19-S at $1\times1011$ VP per dose (n=10),
Cohort 2A—hAd5-COVID-19-S/N at $5\times1010$ VP per dose (n=10),
Cohort 2B—hAd5-COVID-19-S/N at $1\times1011$ VP per dose (n=10).

Each subject will receive a subcutaneous (SC) injection of hAd5-COVID-19-S or hAd5-COVID-19-S/N on Day 1 and Day 22 (ie, 2 doses). This dosing schedule is consistent with hAd5 [E1-, E2b-, E3-] vector-based vaccines currently in clinical trials. Cohorts 1-2 will enroll in parallel and may be opened at the same time or in a staggered manner depending upon investigational product supply. Subjects in cohorts 1A and 2A will complete the low-dose vaccination regimen first. After all subjects in cohorts 1A and 2A have completed at least a single dose and follow-up assessments during the toxicity assessment period through study day 8, enrollment will proceed if ImmunityBio Safety Review Committee (SRC) and at least one qualified infectious disease physician, independent of the Sponsor and trial, confirms absence of safety concerns. Subjects will then be enrolled in higher-dose cohorts 1B and 2B, and vaccinated. For all subjects, follow-up study visits will occur at days 8, 22, 29, 52, and at months 3, 6, and 12 following the final vaccination. Additional follow up for safety information will occur via telephone contact as noted in the Schedule of Events. The primary objectives of the initial safety phase 1b are to evaluate preliminary safety and reactogenicity of the hAd5-COVID-19-S and hAd5-COVID-19-S/N vaccines. The secondary objectives are to evaluate the extended safety and immunogenicity of the hAd5-COVID-19-S and hAd5-COVID-19-S/N vaccines.

Expanded Phase 1b: Safety and Immunogenicity for Construct Selection

Phase 1b expansion will proceed if the SRC determines it is safe to do so based on a review of safety data from the phase 1b safety assessment. In phase 1b expansion, a total of 60 healthy subjects will be divided into 4 dosing cohorts (cohorts 1A, 1B, 2A, 2B; n=15 for each cohort):
Cohort 1A—hAd5-COVID-19-S at $5\times1010$ VP per dose (n=15)
Cohort 1B—hAd5-COVID-19-S at $1\times1011$ VP per dose (n=15)
Cohort 2A—hAd5-COVID-19-S/N at $5\times1010$ VP per dose (n=15)
Cohort 2B—hAd5-COVID-19-S/N at $1\times1011$ VP per dose (n=15)

Each subject will receive a SC injection of hAd5-COVID-19-S or hAd5-COVID-19-S/N on Day 1 and Day 22 (ie, 2 doses). For all subjects, follow-up study visits will occur at days 8, 22, 29, 52, and at months 3, 6, and 12 following the final vaccination. Additional follow up for safety information will occur via telephone contact as noted in the Schedule of Events. The primary objective of the expanded phase 1b is to select the most immunogenic construct between hAd5-COVID-19-S and hAd5-COVID-19-S/N and dose level as determined by changes in humoral and cellular immunogenicity indexes. The secondary objectives are to assess safety and reactogenicity of hAd5-COVID-19-S and hAd5-COVID-19-S/N.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). Most preferably, the recombinant virus is administered via subcutaneous or subdermal injection. However, in other contemplated aspects, administration may also be intravenous injection. Alternatively, or additionally, antigen presenting cells may be isolated or grown from cells of the patient, infected in vitro, and then transfused to the patient.

In one aspect of any of the embodiments described above or elsewhere herein, the composition is formulated in a pharmaceutically acceptable excipient suitable for administration to a subject.

It is still further contemplated that the recombinant viruses and yeasts contemplated herein may further comprises a sequence that encodes at least one of a co-stimulatory molecule, an immune stimulatory cytokine, and a protein that interferes with or down-regulates checkpoint inhibition. For example, suitable co-stimulatory molecules include CD80, CD86, CD30, CD40, CD30L, CD40L, ICOS-L, B7-H3, B7-H4, CD70, OX40L, 4-1BBL, GITR-L, TIM-3, TIM-4, CD48, CD58, TL1A, ICAM-1, and/or LFA3, while suitable immune stimulatory cytokine include IL-2, IL-12, IL-15, IL-15 super agonist (N803), IL-21, IPS1, and/or LMP1, and/or suitable proteins that interfere include antibodies against or antagonists of CTLA-4, PD-1, TIM1 receptor, 2B4, and/or CD160.

It should be appreciated that all of the above noted co-stimulatory genes are well known in the art, and sequence information of these genes, isoforms, and variants can be retrieved from various public resources, including sequence data bases accessible at the NCBI, EMBL, GenBank, RefSeq, etc. Moreover, while the above exemplary stimulating molecules are preferably expressed in full length form as expressed in human, modified and non-human forms are also deemed suitable so long as such forms assist in stimulating or activating T-cells. Therefore, muteins, truncated forms and chimeric forms are expressly contemplated herein.

The immunotherapeutic compositions disclosed herein may be either "prophylactic" or "therapeutic". When provided prophylactically, the compositions of the present disclosure are provided in advance of the development of, or the detection of the development of, a coronavirus disease, with the goal of preventing, inhibiting or delaying the development of the coronavirus disease; and/or generally preventing or inhibiting progression of the coronavirus disease in an individual. Therefore, prophylactic compositions can be administered to individuals that appear to be coronavirus disease free (healthy, or normal, individuals), or to individuals who has not yet been detected of coronavirus. Individuals who are at high risk for developing a coronavirus disease, may be treated prophylactically with a composition of the instant disclosure.

When provided therapeutically, the immunotherapy compositions are provided to an individual who is diagnosed with a coronavirus disease, with the goal of ameliorating or curing the coronavirus disease; increasing survival of the individual; preventing, inhibiting, reversing or delaying development of coronavirus disease in the individual.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the disclosures herein, and does not pose a limitation on the scope of the invention otherwise claimed. No language in the specification should be construed as indicating any non-claimed element essential to the practice of the claimed invention.

Many more modifications besides those already described are possible without departing from the concepts disclosed herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method for inducing immunity in an individual, the method comprising administration to the individual a replication defective adenoviral serotype-5 (Ad5) vector comprising 1) an E1 gene region deletion, 2) an E2b gene region deletion, 3) a nucleic acid sequence that encodes a SARS-COV-2 S protein having the amino acid sequence of SEQ ID NO: 4, and 4) a nucleic acid sequence that encodes a chimeric protein comprising a SARS-COV-2 N protein having the amino acid sequence of SEQ ID NO: 1 and an endosomal targeting sequence having the amino acid sequence of SEQ ID NO: 2.

2. The method of claim 1, further comprising administering a co-stimulatory molecule and/or an immune stimulatory cytokine.

3. The method of claim 2, wherein the co-stimulatory molecule is selected from the group consisting of CD80, CD86, CD30, CD40, CD30L, CD40L, ICOS-L, B7-H3, B7-H4, CD70, OX40L, 4-IBBL, GITR-L, TIM-3, TIM-4, CD48, CD58, TLIA, ICAM-1, and LFA3.

4. The method of claim 2, wherein the immune stimulatory cytokine is selected from the group consisting of IL-2, IL-12, IL-15, nogapendekin alfa-imbakicept, IL-21, IPS1, and LMP 1.

5. The method of claim 1, wherein the individual is administered $1\times10^{10}$ to $1\times10^{11}$ viral particles (VP) per dose.

6. The method of claim 1, wherein the Ad5 vector is administered orally, subcutaneously, or intravenously.

7. A method for preventing and/or treating COVID-19 in an individual, the method comprising administration to the individual a replication defective adenoviral serotype-5 (Ad5) vector comprising 1) an E1 gene region deletion, 2) an E2b gene region deletion, 3) a nucleic acid sequence comprising a portion that encodes a SARS-COV-2 S protein having the amino acid sequence of SEQ ID NO: 4; and 4) a nucleic acid sequence that encodes a chimeric protein comprising a SARS-COV-2 N protein having the amino acid sequence of SEQ ID NO: 1, and an endosomal targeting sequence having the amino acid sequence of SEQ ID NO: 2.

8. The method of claim 7, further comprising administering a co-stimulatory molecule and/or an immune stimulatory cytokine.

9. The method of claim 8, wherein the co-stimulatory molecule is selected from the group consisting of CD80, CD86, CD30, CD40, CD30L, CD40L, ICOS-L, B7-H3, B7-H4, CD70, OX40L, 4-IBBL, GITR-L, TIM-3, TIM-4, CD48, CD58, TLIA, ICAM-1, and LFA3.

10. The method of claim 8, wherein the immune stimulatory cytokine is selected from the group consisting of IL-2, IL-12, IL-15, nogapendekin alfa-imbakicept, IL-21, IPS1, and LMP1.

11. The method of claim 7, wherein the individual is administered $1\times10^{10}$ to $1\times10^{11}$ viral particles (VP) per dose.

12. The method of claim 7, wherein the Ad5 vector is administered orally, subcutaneously, or intravenously.

* * * * *